(12) United States Patent
Tallon et al.

(10) Patent No.: US 10,632,059 B2
(45) Date of Patent: Apr. 28, 2020

(54) NON-AQUEOUS COMPOSITIONS OF POLYMERS DERIVED FROM MONOMERS HAVING ACRYLOYL MOIETY AND LACTAM MOIETY AND APPLICATIONS THEREOF

(71) Applicant: ISP INVESTMENTS LLC, Wilmington, DE (US)

(72) Inventors: Michael A. Tallon, Aberdeen, NJ (US); Donald I. Prettypaul, Englewood, NJ (US); Drupesh Patel, Lake Hiawatha, NJ (US); Mousumi Ghosh, Elmwood Park, NJ (US); Osama M. Musa, Kinnelon, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 15/777,785

(22) PCT Filed: Nov. 17, 2016

(86) PCT No.: PCT/US2016/062489
§ 371 (c)(1),
(2) Date: May 21, 2018

(87) PCT Pub. No.: WO2017/087645
PCT Pub. Date: May 26, 2017

(65) Prior Publication Data
US 2018/0333345 A1 Nov. 22, 2018

Related U.S. Application Data

(60) Provisional application No. 62/257,980, filed on Nov. 20, 2015.

(51) Int. Cl.
| | |
|---|---|
| *A61K 8/81* | (2006.01) |
| *C08F 222/22* | (2006.01) |
| *C08F 222/38* | (2006.01) |
| *A61Q 17/04* | (2006.01) |

(52) U.S. Cl.
CPC ............ *A61K 8/8152* (2013.01); *A61K 8/817* (2013.01); *A61K 8/8182* (2013.01); *A61Q 17/04* (2013.01); *C08F 222/22* (2013.01); *C08F 222/38* (2013.01); *A61K 2800/31* (2013.01)

(58) Field of Classification Search
CPC .............................. A61K 8/817; A61K 8/8182
See application file for complete search history.

(56) References Cited

U.S. PATENT DOCUMENTS

| | | | | |
|---|---|---|---|---|
| 2,882,262 A | * | 4/1959 | Smith ................... | G03F 7/0125 526/264 |
| 5,196,495 A | * | 3/1993 | Chuang ................ | A61K 8/8158 526/264 |
| 5,275,811 A | * | 1/1994 | Chuang ................ | A61K 8/8158 424/70.16 |
| 5,730,966 A | | 3/1998 | Torgerson et al. | |

(Continued)

FOREIGN PATENT DOCUMENTS

| | | | |
|---|---|---|---|
| WO | WO-9723523 A1 * | 7/1997 | ............. A61L 27/16 |
| WO | WO-2011063208 A1 * | 5/2011 | ............ C08F 222/40 |
| WO | WO2015153461 A1 | 10/2015 | |

OTHER PUBLICATIONS

International Search Report, PCT/US2016/062489 published on May 26, 2017.

*Primary Examiner* — Nicole M. Buie-Hatcher
(74) *Attorney, Agent, or Firm* — William J. Davis; Nathalie Tietcheu

(57) ABSTRACT

The invention provides non-aqueous compositions comprising film forming polymers comprising repeating units derived from: (a) at least one monomer comprising at least one functionalized or unfunctionalized acryloyl moiety and at least one lactam moiety; (b) at least one monomer selected from the group consisting of functionalized and unfunctionalized $C_1$-$C_7$ alkyl (alk)acrylates, $C_1$-$C_7$ alkyl (alk)acrylamides, and combinations thereof; and (c) at least one monomer selected from the group consisting of functionalized and unfunctionalized $C_8$-$C_{60}$ alkyl (alk)acrylates, $C_8$-$C_{60}$ (alk) alkyl acrylamides, and combinations thereof. The invention further provides applications of these compositions in various industrial arts, particularly in personal care. The invention furthermore provides water-resistant non-aqueous personal care compositions. Variables a, b and c are described herein.

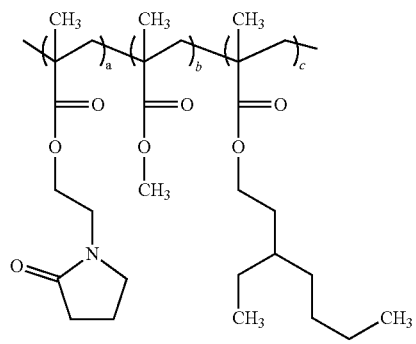

2 Claims, 5 Drawing Sheets

(56) References Cited

U.S. PATENT DOCUMENTS

| | | |
|---|---|---|
| 6,207,778 B1 | 3/2001 | Jachowicz et al. |
| 10,233,276 B2 * | 3/2019 | Tallon .................... A61K 47/34 |
| 2002/0185222 A1 | 12/2002 | Wigdorski et al. |
| 2005/0249686 A1 * | 11/2005 | Pataut ...................... A61K 8/31 |
| | | 424/70.1 |
| 2010/0166985 A1 * | 7/2010 | Brockmeyer ......... C08F 220/18 |
| | | 428/32.1 |
| 2013/0150481 A1 * | 6/2013 | Hood .................... C08F 220/36 |
| | | 522/120 |

* cited by examiner

NON-AQUEOUS COMPOSITIONS OF POLYMERS DERIVED FROM MONOMERS HAVING ACRYLOYL MOIETY AND LACTAM MOIETY AND APPLICATIONS THEREOF

BACKGROUND

Field of the Invention

The invention provides non-aqueous, compositions of film forming polymers comprising repeating units derived from monomers having at least one functionalized or unfunctionalized acryloyl moiety and at least one lactam moiety. The invention further provides applications of the non-aqueous compositions in various industrial arts, particularly in personal care. The invention furthermore provides water-resistant non-aqueous personal care compositions, particularly sun care compositions.

Description of Related Art

U.S. Pat. No. 2,882,262 discloses N-(acryloxyalkyl)- and N-(methacryloxyalkyl)-2-pyrrolidones, polymers thereof, and a process for their preparation. The polymers are particularly useful in the photographic art.

U.S. published patent application 2010/0166985 discloses aqueous dispersions of (meth)acrylic esters of polymers comprising N-hydroxyalkylated lactam units, processes for preparing them, and use of (meth)acrylic esters of polymers comprising N-hydroxyalkylated lactam units for treating paper.

U.S. published patent application 2007/0238807 discloses film forming compositions having a polymer and optionally a bioactive agent in a solvent, where the compositions can be used for various applications, such as a "liquid bandage" to form a water resistant film for covering and protecting injuries to a biological surface.

EP 2610332 A1 discloses a lubricating composition containing an oil of lubricating viscosity and a star polymer that has at least two inner blocks, at least one of which is in turn bonded to one or more outer blocks which relates to methods of lubricating a mechanical device with the lubricating composition. Disclosed in this application are oxygen containing monomeric compounds such as N-methacryloyl-2-pyrrolidone, N-(2-methacryloyloxyethyl)-2-pyrrolidone, N-(3-methacryloyloxypropyl)-2-pyrrolidone, N-(2-methacryloyoyloxypentadecyl)-2-pyrrolidone, and N-(3-methacryloyloxyheptadecyl)-2-pyrrolidone. However, the star polymer architecture, derived from and inner and outer block polymer construct, is distinct from the current invention. The preparation and utility of linear film forming copolymers derived from (a) at least one monomer comprising at least one functionalized or unfunctionalized acryloyl moiety and at least one lactam moiety; (b) at least one monomer selected from the group consisting of functionalized and unfunctionalized $C_1$-$C_7$ alkyl (alk)acrylates, $C_1$-$C_7$ alkyl (alk)acrylamides, and combinations thereof; and (c) at least one monomer selected from the group consisting of functionalized and unfunctionalized $C_8$-$C_{60}$ alkyl (alk)acrylates, $C_8$-$C_{60}$ (alk)alkyl acrylamides, and combinations thereof is not disclosed.

U.S. Pat. No. 4,584,192 discloses a film-forming composition containing an antimicrobial agent and methods of use. The film-forming composition comprises (a) a film-forming copolymer consisting essentially of copolymerized A, B, and C monomers as follows: A is a monomeric acrylic or methacrylic acid ester of an alkyl alcohol containing a single hydroxyl, the alcohol being further described as having from 2 to about 14 carbon atoms when the A monomer is an acrylic acid ester, and about 7 to 18 carbon atoms when the A monomer is a methacrylic acid ester, the amount by weight of A monomer being about 15 to 80% of the total weight of all monomers in the copolymer; B is a monomeric methacrylic acid ester of an alkyl alcohol containing a single hydroxyl, the alcohol being further described as having from 1 to about 6 carbon atoms, the amount by weight of B monomer being about 20 to 70% of the total weight of all monomers in the copolymer; and C is an N-vinyl lactam, the amount by weight of which being about 1 to 15% of the total weight of all monomers in the copolymer; (b) an effective amount of a broad spectrum antimicrobial agent; the composition being dermatologically-acceptable, and, when applied to skin from a fugitive solvent, being capable of forming a clear, substantially fluid-resistant, substantially tack-free, flexible film which adheres to skin and releases the antimicrobial agent to skin.

U.S. published patent application 2008/0138300 discloses a cosmetic composition comprising, in a cosmetically acceptable medium: at least one acrylic polymer resulting from the copolymerization of: a) at least one monomer A chosen from esters derived from the reaction of (meth) acrylic acid with at least one monoalcohol comprising from 2 to 20 carbon atoms, b) at least one monomer B chosen from esters derived from the reaction of methacrylic acid with at least one monoalcohol comprising from 1 to 10 carbon atoms, and c) at least one monomer C chosen from N-vinyllactams and derivatives thereof, and at least one organic solvent phase comprising at least one first organic solvent, wherein the at least one organic solvent phase comprises less than or equal to 15% by weight of solvents chosen from lower monoalcohols comprising from 1 to 5 carbon atoms and $C_3$-$C_4$ ketones, relative to the total weight of the composition. Monomer C is present in a numerical proportion ranging from 1% to 15% relative to the total number of monomers in the polymer.

We have found that non-aqueous film forming compositions according to the invention provide, among many other benefits, the important benefits of enhanced water-resistance. The compositions may be formulated for many applicatons, non-limiting examples of which include personal care, sun care, pharmaceuticals, adhesives, energy, coatings, and agricultural.

SUMMARY

In a first aspect, the invention provides a non-aqueous composition comprising a film forming polymer comprising repeating units derived from at least: (a) at least one monomer comprising at least one functionalized or unfunctionalized acryloyl moiety and at least one lactam moiety; (b) at least one monomer selected from the group consisting of functionalized and unfunctionalized $C_1$-$C_7$ alkyl (alk)acrylates, $C_1$-$C_7$ alkyl (alk)acrylamides, and combinations thereof; and (c) at least one monomer selected from the group consisting of functionalized and unfunctionalized $C_8$-$C_{60}$ alkyl (alk)acrylates, $C_8$-$C_{60}$ alkyl (alk)acrylamides, and combinations thereof. Particular, yet non-limiting examples of non-aqueous compositions include personal care compositions, coating compositions, household, industrial and institutional compositions, pharmaceutical compositions, food compositions, cementing fluids, oilfield compositions, construction compositions, servicing fluids, gravel packing muds, fracturing fluids, completion fluids, workover fluids, spacer fluids, drilling muds, biocides, adhesives, inks, papers, polishes, membranes, metal working fluids, plastics, textiles, printing compositions, lubricants, preservatives, agrochemicals, and wood-care compositions.

In a second aspect, the invention provides a non-aqueous personal care composition comprising a film forming polymer comprising repeating units derived from at least: (a) at least one monomer comprising at least one functionalized or unfunctionalized acryloyl moiety and at least one lactam moiety; (b) at least one monomer selected from the group consisting of functionalized and unfunctionalized $C_1$-$C_7$ alkyl (alk)acrylates, $C_1$-$C_7$ alkyl (alk)acrylamides, and combinations thereof; and (c) at least one monomer selected from the group consisting of functionalized and unfunctionalized $C_8$-$C_{60}$ alkyl (alk)acrylates, $C_8$-$C_{60}$ alkyl (alk)acrylamides, and combinations thereof. Particular, yet non-limiting examples of non-aqueous personal care compositions include sun care compositions, face care compositions, lip care compositions, eye care compositions, skin care compositions, after-sun compositions, body care compositions, nail care compositions, anti-aging compositions, insect repellants, oral care compositions, deodorant compostions, hair care compositions, conditioning compositions, color cosmetic compositions, color-protection compositions, self-tanning compositions, and foot care compositions.

DETAILED DESCRIPTION

Figure 1:
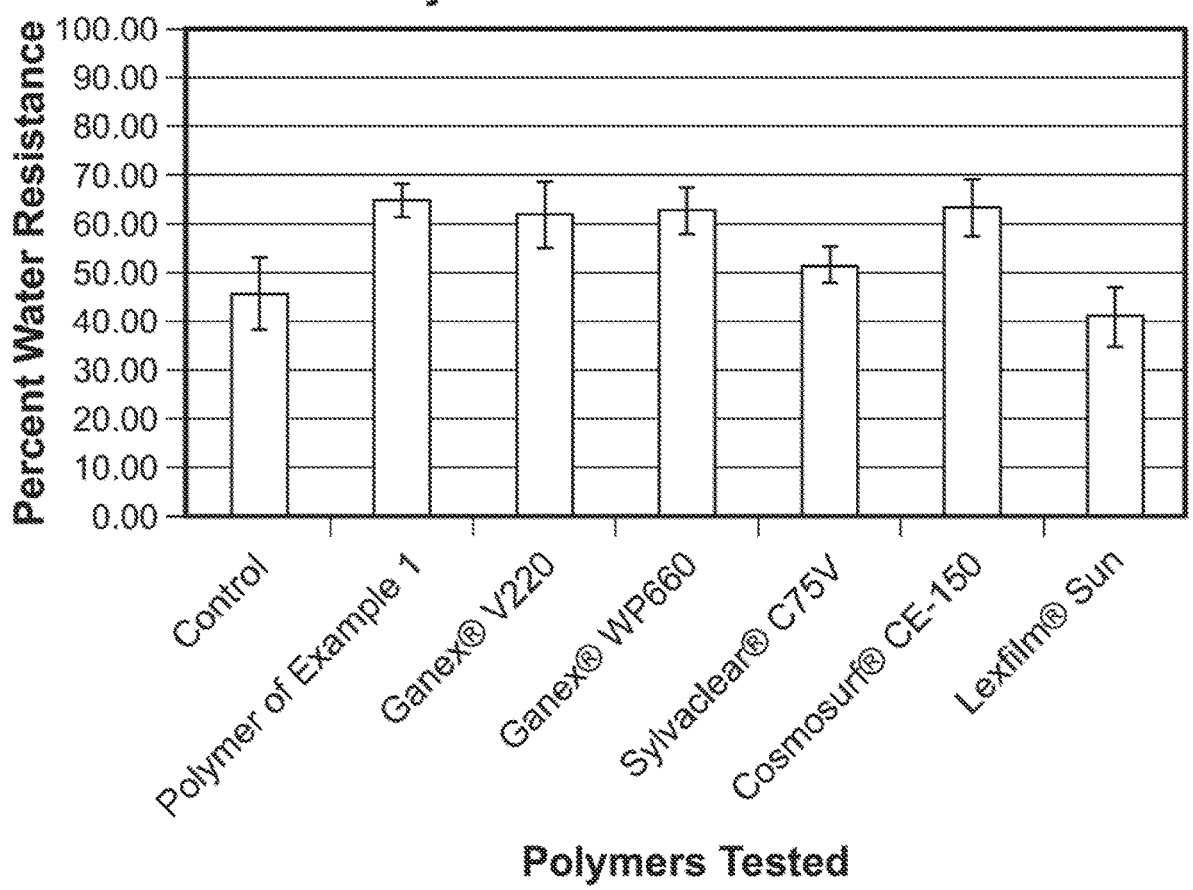
FIG. 1 shows the percent water resistance study of non-aqueous sun care formulations according to the invention in comparison with various commercially available formulations.

Before explaining at least one aspect of the disclosed and/or claimed inventive concept(s) in detail, it is to be understood that the disclosed and/or claimed inventive concept(s) is not limited in its application to the details of construction and the arrangement of the components or steps or methodologies set forth in the following description or illustrated in the drawings. The disclosed and/or claimed inventive concept(s) is capable of other aspects or of being practiced or carried out in various ways. Also, it is to be understood that the phraseology and terminology employed herein is for the purpose of description and should not be regarded as limiting.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

All of the articles and/or methods disclosed herein can be made and executed without undue experimentation in light of the present disclosure. While the articles and methods of the disclosed and/or claimed inventive concept(s) have been described in terms of particular aspects, it will be apparent to those of ordinary skill in the art that variations may be applied to the articles and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed and/or claimed inventive concept(s).

As utilized in accordance with the disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, $B_{Xn}$, $B_{Xn+1}$, or combinations thereof" is intended to include at least one of: A, $B_{Xn}$, $B_{Xn+1}$, $AB_{Xn}$, A $B_{Xn+1}$, $B_{Xn}B_{Xn+1}$, or $AB_{Xn}B_{Xn+1}$ and, if order is important in a particular context, also $B_{Xn}A$, $B_{Xn+1}A$, $B_{Xn+1}B_{Xn}A$, $B_{Xn+1}B_{Xn}A$, $B_{Xn}B_{Xn+1}A$, $AB_{Xn+1}B_{Xn}$, $B_{Xn}AB_{Xn+1}$, or $B_{Xn+1}AB_{Xn}$. Continuing with this example, expressly included are combinations that contain repeats of one or more item or term, such as $B_{Xn}B_{Xn}$, AAA, $MB_{Xn}$, $B_{Xn}B_{Xn}B_{Xn+1}$, $AAAB_{Xn}B_{Xn+1}B_{Xn+1}B_{Xn+1}$ $B_{Xn+1}$, $B_{Xn+1}B_{Xn}B_{Xn}AAA$, $B_{Xn+1}A$ $B_{Xn}AB_{Xn}B_{Xn}$, and so forth. The skilled artisan will understand that typically there is no limit on the number of items or terms in any combination, unless otherwise apparent from the context.

The term "each independently selected from the group consisting of" means when a group appears more than once in a structure, that group may be selected independently each time it appears.

The term "hydrocarbyl" includes straight-chain and branched-chain alkyl, alkenyl, alkynyl, cycloalkyl, cycloalkenyl, aryl groups, and combinations thereof with optional heteroatom(s). A hydrocarbyl group may be mono-, di- or polyvalent.

The term "alkyl" refers to a functionalized or unfunctionalized monovalent straight-chain, branched-chain or cyclic $C_1$-$C_{60}$ group optionally having one or more heteroatoms. Particularly, an alkyl is a $C_1$-$C_{45}$ group and more particularly, a $C_1$-$C_{30}$ group. Particular, yet non-limiting examples of alkyl groups include methyl, ethyl, n-propyl, isopropyl, n-butyl, isobutyl, tert-butyl, cyclobutyl, n-pentyl, isopentyl, cyclopentyl, n-hexyl, cyclohexyl, n-heptyl, cyclyheptyl, methylcyclohexyl, n-octyl, 2-ethylhexyl, tert-octyl, iso-norbornyl, n-dodecyl, tert-dodecyl, n-tetradecyl, n-hexadecyl, n-octadecyl, and n-eicosyl.

The term "alkylene" refers to a functionalized or unfunctionalized divalent straight-chain, branched-chain or cyclic $C_1$-$C_{40}$ group optionally having one or more heteroatoms. Particularly, an alkylene is a $C_1$-$C_{45}$ group and more particularly, a $C_1$-$C_{30}$ group. Particular, yet non-limiting examples of alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —$CH_2$—$CH_2$—$CH_2$—$CH_2$—$CH_2$—$CH_2$—$CH_2$—, cyclopropylene, cyclobutylene, cyclopentylene, cyclohexylene, and the like.

The term "heteroatom" refers to oxygen, nitrogen, sulfur, silicon, phosphorous, and/or halogen. The heteroatom(s) may be present as a part of one or more heteroatom-containing functional groups and/or as a part of one or more heterocyclic rings. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups.

The term "halogen" refers to chloro, bromo, iodo and/or fluoro.

The term "metal ion" includes alkali metal ions, alkaline earth metal ions, and transition metal ions. For example, sodium, calcium, copper and iron derived ions.

The term "ammonium" includes protonated $NH_3$ and protonated primary, secondary, and tertiary organic amines.

The term "functionalized" refers to the state of a moiety that has one or more functional groups introduced to it by way of one or more functionalization reactions known to a person having ordinary skill in the art. Particular, yet non-limiting examples of functionalization reactions include epoxidation, sulfonation, hydrolysis, amidation, esterification, hydroxylation, dihyroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like. Particularly, functionalization of a moiety replaces one or more hydrogens in the moiety with one or more non-hydrogen groups, for e.g., alkyl, alkoxyl, cycloalkyl, alkenyl, cycloalkenyl, alkynyl, and/or aryl groups. Particular, yet non-limiting examples of cycloalkyl groups include cyclopentane, cyclohexane, cycloheptane, and the like. Particular, yet non-limiting examples of alkoxy groups include methoxy, ethoxy, n-propoxy, isopropoxy, and the like. Particular, yet non-limiting examples of aryl groups include benzenes, naphthalenes (2 rings), anthracenes (3 rings), and the like.

The term "residue of" refers to a fragment of a reactant that remains after a reaction with another reactant(s). The residue may be mono-, di- or polyvalent.

The term "monomer" refers to a small molecule that chemically bonds during polymerization to one or more monomers of the same or different kind to form a polymer.

The term "polymer" refers to a large molecule comprising one or more types of monomer residues (repeating units) connected by covalent chemical bonds. By this definition, polymer encompasses compounds wherein the number of monomer units may range from very few, which more commonly may be called as oligomers, to very many. Non-limiting examples of polymers include homopolymers, and non-homopolymers such as copolymers, terpolymers, tetrapolymers and the higher analogues. The polymer may have a random, block, and/or alternating architecture.

The term "homopolymer" refers to a polymer that consists essentially of a single monomer type.

The term "non-homopolymer" refers to a polymer that comprises more than one monomer types.

The term "copolymer" refers to a non-homopolymer that comprises two different monomer types.

The term "terpolymer" refers to a non-homopolymer that comprises three different monomer types.

The term "branched" refers to any non-linear molecular structure. The term includes both branched and hyper-branched structures.

The term "free radical addition polymerization initiator" refers to a compound used in a catalytic amount to initiate a free radical addition polymerization. The choice of initiator depends mainly upon its solubility and its decomposition temperature.

The term "alkyl (alk) acrylate" refers to an alkyl ester of an acrylic acid or an alkyl acrylic acid.

The term "alkyl (alk) acrylamide" refers to an alkyl amide of an acrylic acid or an alkyl acrylic acid.

The term "acryloyl" refers to a moiety having the generic structure:

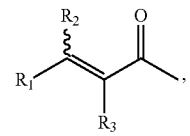

wherein each $R_1$, $R_2$, and $R_3$ is independently selected from the group consisting of hydrogen and functionalized and unfunctionalized alkyl, alkenyl, aryl, nitrile, formyl, carboxyl, carboxylate salt, carboxylic ester, carboxamide, halogen, thiocarboxylate, and combinations thereof.

The term "non-aqueous" refers to a state of not being aqueous in nature.

By "non-aqueous" it is generally meant that water is not deliberately added to the composition in any significant quantity. However, the term "non-aqueous" does not mean that small amounts of water cannot be present, for example as a consequence of its association with hygroscopic raw materials. Accordingly, for the purposes of this invention, the term "non-aqueous" generally means that water is present in an amount no greater than about 5%, more preferably no greater than about 3% by weight based on the total weight of the composition.

The term "film forming" refers to the capability of a substance to form, or evolve into a structure, that is primarily, but not necessarily, a continuous thin sheet of said substance which may or may not be in contact with a substrate. For example, a 10% aqueous solution of poly (vinyl pyrrolidone) (PVP K-90), when cast with a #38 Meyer rod onto a substrate (i.e. Melinex film), exhibits film formation upon drying (evaporation of water).

The terms "personal care composition" and "cosmetics" refer to compositions intended for use on or in the human body, such as skin, sun, hair, oral, cosmetic, and preservative compositions, including those to alter the color and appearance of the skin and hair.

The phrase "pharmaceutically acceptable" or "cosmetically acceptable" refers to molecular entities and compositions that are generally regarded as safe. Particularly, as used herein, the term "pharmaceutically acceptable" or "cosmetically acceptable" means approved by a regulatory agency of the appropriate governmental agency or listed in the U.S. Pharmacopoeia or other generally recognized pharmacopoeia for use in animals, and more particularly in humans.

The term "keratinous substrate" refers to human keratinous surface, and may be chosen from, for example, hair, eyelashes, and eyebrows, as well as the skin and nails. Other mammels are also envisioned.

The term "turbidity" refers to the cloudiness or haziness of a fluid. Turbidity or haze (or haziness) is scattering of light by a medium, which results into cloudy appearance, and poorer clarity of objects when viewing through that. The turbidity is caused by individual particles (suspended solids) that are generally invisible to the naked eye. These particles scatter incoming light and turbidity can be measured by using an instrument called a nephelometer with the detector setup to the side of the light beam. The units of turbidity from a calibrated nephelometer are called Nephelometric Turbidity Units (NTU).

The term "sun care composition" refers to any composition intended for use on the human body for protection from harmful or undesirable radiation from the sun.

The term "pharmaceutical composition" refers to any composition comprising at least one pharmaceutically active ingredient, as well as any product which results, directly or indirectly, from combination, complexation, or aggregation of any two or more of the ingredients, from dissociation of one or more of the ingredients, or from other types of reactions or interactions of one or more of the ingredients.

The term "pharmaceutically active ingredient" should be construed in a broad sense as including any ingredient considered to have a therapeutic effect when delivered to a subject in need thereof and further being regulated by drug authorities like CDER, EMEA, TAG etc. Pharmaceutically active ingredients may act systemically upon oral consumption, or locally such as when present in the buccal cavity, on the skin, etc. They may also be delivered across the skin as in transdermal drug delivery systems.

All percentages, ratio, and proportions used herein are based on a weight basis unless otherwise specified.

In a first aspect, the invention provides a non-aqueous composition comprising a film forming polymer comprising repeating units derived from at least: (a) at least one monomer comprising at least one functionalized or unfunctionalized acryloyl moiety and at least one lactam moiety (monomer A); (b) at least one monomer (monomer $B_{X1}$) selected from the group consisting of functionalized and unfunctionalized $C_1$-$C_7$ alkyl (alk)acrylates, $C_1$-$C_7$ alkyl (alk)acrylamides, and combinations thereof; and (c) at least one monomer (monomer $B_{X2}$) selected from the group consisting of functionalized and unfunctionalized $C_8$-$C_{60}$ alkyl (alk)acrylates, $C_8$-$C_{60}$ alkyl (alk)acrylamides, and combinations thereof.

In particular embodiments, the monomer (monomer A) having at least one functionalized or unfunctionalized acryloyl moiety and at least one lactam moiety has a structure:

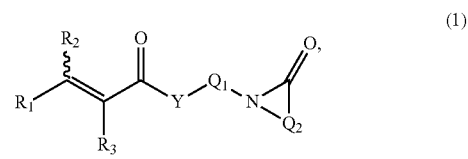

wherein each $R_1$ $R_2$ and $R_3$ is independently selected from the group consisting of hydrogen, halogens, functionalized and unfunctionalized $C_1$-$C_4$ alkyl, and

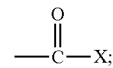

each X is independently selected from the group consisting of $OR_4$, OM, halogen, $N(R_5)(R_6)$,

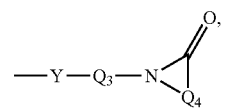

and combinations thereof; each Y is independently oxygen, $NR_7$ or sulfur; each $R_4$, $R_5$, $R_6$ and $R_7$ is independently selected from the group consisting of hydrogen and functionalized and unfunctionalized alkyl; each M is independently selected from the group consisting of metal ions, ammonium ions, organic ammonium cations, and combinations thereof; and each $Q_1$, $Q_2$, $Q_3$, and $Q_4$ is independently selected from the group consisting of functionalized and unfunctionalized alkylene.

Particularly, each $Q_1$, $Q_2$, $Q_3$, and $Q_4$ is independently selected from the group consisting of functionalized and unfunctionalized $C_1$-$C_{12}$ alkylene. Particular, yet non-limiting examples of alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, and —$CH_2$—$CH_2$—$CH_2$—$CH_2$—$CH_2$—$CH_2$—$CH_2$—.

In one non-limiting embodiment, each $R_1$, $R_2$ and $R_3$ is independently selected from the group consisting of hydrogen, methyl and combinations thereof. Particularly, $R_1$ and $R_2$ are hydrogens and $R_3$ is hydrogen or methyl.

In another non-limiting embodiment, each $R_1$ and $R_3$ is independently hydrogen or methyl; $R_2$ is

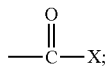

X is selected from the group consisting of $OR_4$, OM, halogens, and $N(R_5)(R_6)$; each $R_4$, $R_5$, and $R_6$ is independently selected from the group consisting of hydrogen and functionalized and unfunctionalized alkyl; and each M is independently selected from the group consisting of metal ions, ammonium ions, organic ammonium cations, and combinations thereof. Particularly, $R_1$ and $R_3$ are hydrogens and $R_2$ is

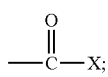

X is selected from the group consisting of $OR_4$, OM and $N(R_5)(R_6)$; each $R_4$, $R_5$, and $R_6$ is independently selected from the group consisting of hydrogen and functionalized and unfunctionalized $C_1$-$C_4$ alkyl; and each M is independently selected from the group consisting of metal ions, ammonium ions, organic ammonium cations, and combinations thereof.

The first polymerizable unit, defined by structure (1), maybe be synthesized using methods recorded in the art, e.g., by reaction of an N-hydroxylalkyl lactam with an acrylate, (meth)acrylate, anhydride, or similar compounds. Production methods include thos decribed in U.S. Pat. Nos. 2,882,262; 5,523,340; 6,369,163; U.S. Patent Application Publication 2007/123673; GB 924,623; 930,668; and 1,404,989; WO 03/006569; and EP 385918. Each of the previous disclosures are hereby incorporated herein by reference in its entirety.

The lactam-containing monomers shown in structures (2)-(57) can be obtained from condensation reactions that include an N-hydroxyalkyl lactam and an unsaturated carboxylic acid, an acrylate, a (meth)acrylate, or an anhydride. Suitable N-hydroxyalkyl lactams include N-hydroxymethyl pyrrolidone and caprolactam, N-hydroxyethyl pyrrolidone and caprolactam, and N-hydroxypropyl pyrrolidone and caprolactam. Non-limiting examples of carboxylic acids that can be used include: acrylic acid, methacrylic acid, itaconic acid, crotonic acid, fumaric acid, succinic acid, and maleic acid. Similarly, acrylates and (meth)acrylates include (without limitation) methyl, ethyl, butyl, octyl, ethyl hexyl acrylates and their (meth)acrylate analogues. Representative anhydrides include formic anhydride, succinic anhydride, maleic anhydride and acetic anhydride.

In particular embodiments, the monomer having at least one functionalized or unfunctionalized acryloyl moiety and at least one lactam moiety has a structure selected from the group consisting of:

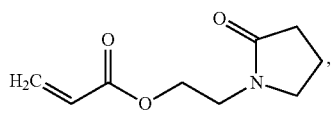
(2)

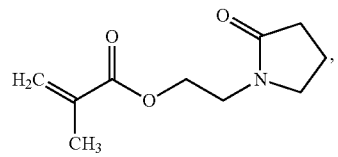
(3)

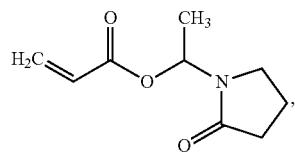
(4)

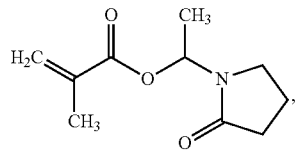
(5)

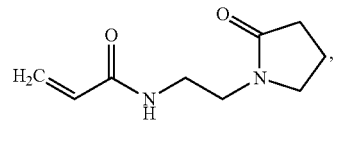
(6)

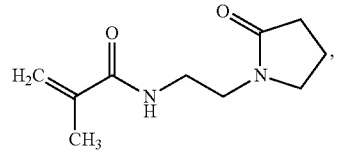
(7)

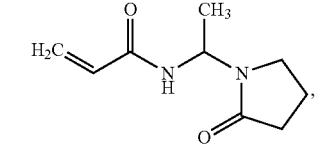
(8)

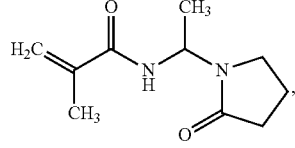
(9)

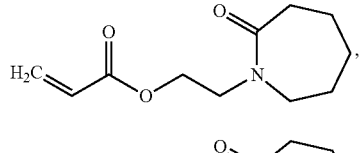
(10)

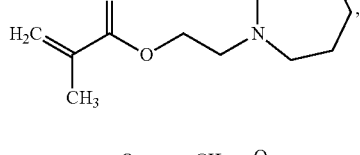
(11)

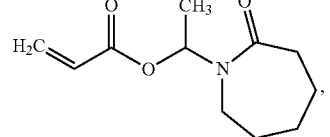
(12)

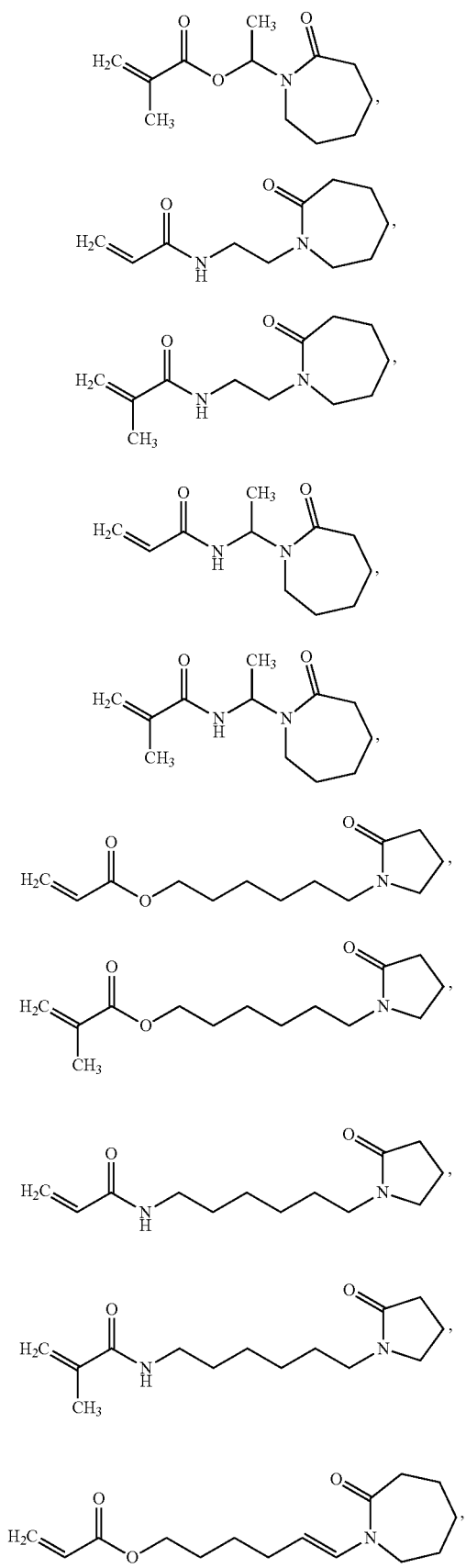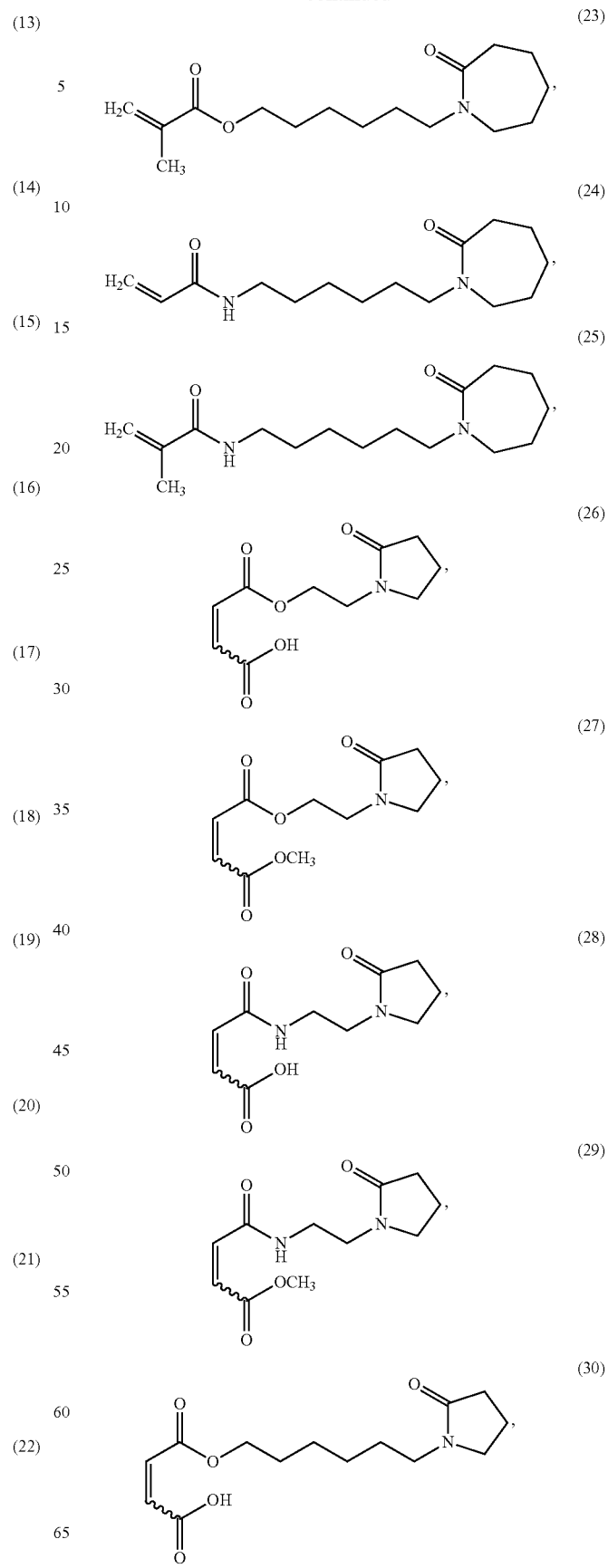

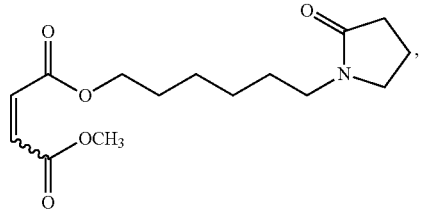 (31)
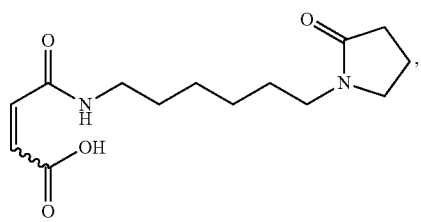 (32)
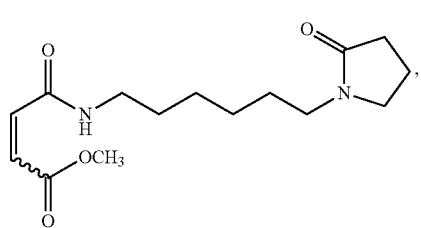 (33)
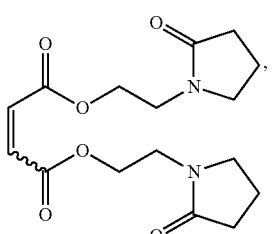 (34)
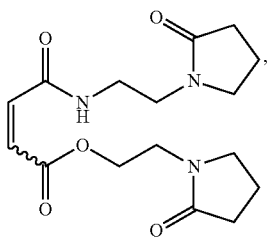 (35)
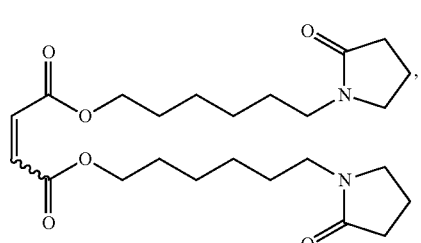 (36)
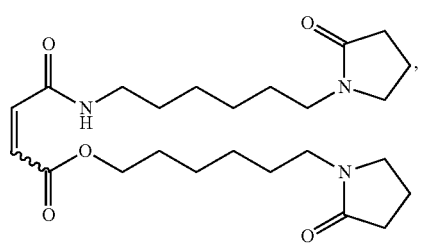 (37)
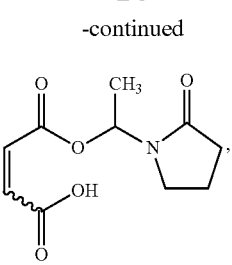 (38)
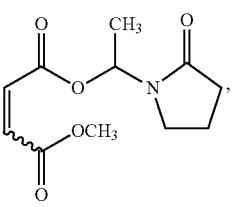 (39)
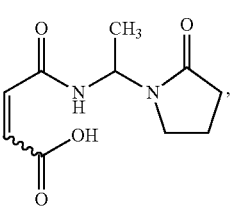 (40)
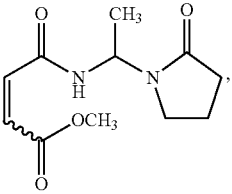 (41)
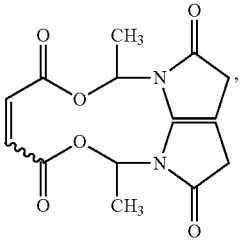 (42)
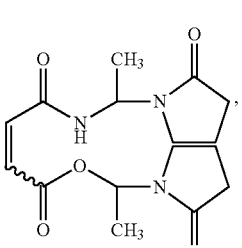 (43)
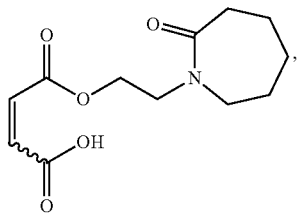 (44)

15
-continued

(45) 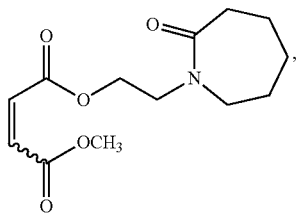

(46) 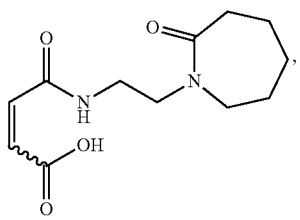

(47) 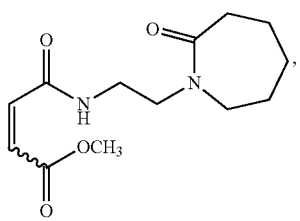

(48) 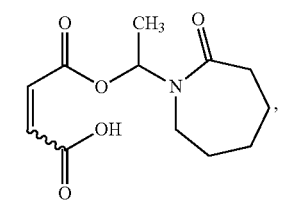

(49) 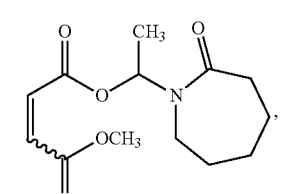

(50) 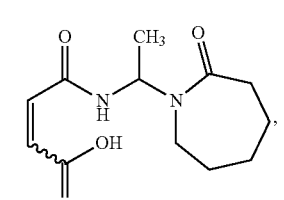

(51) 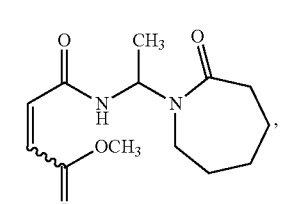

16
-continued

(52) 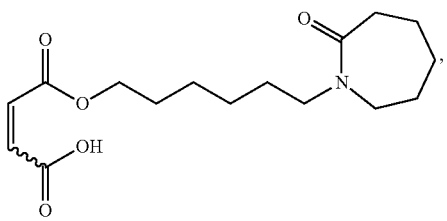

(53) 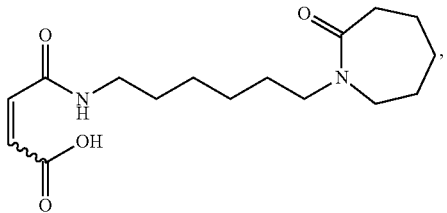

(54) 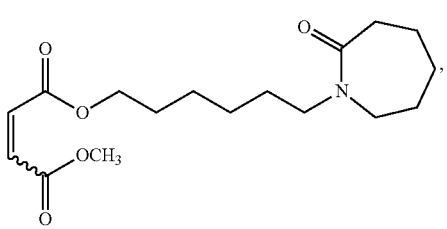

(55) 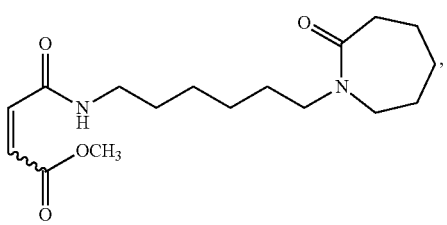

(56) 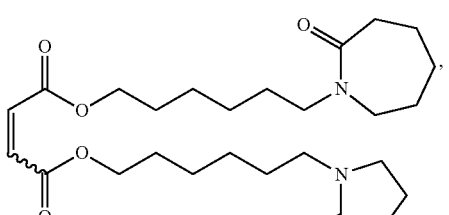

and

(57) 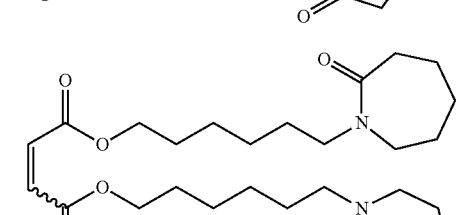

Other suitable examples of can be found in WO 2011/063208, the disclosure of which is hereby incorporated herein by reference in its entirety.

Particular, yet non-limiting examples of $C_1$-$C_7$ alkyl (alk) acrylates (monomer $B_{X1}$) include methyl acrylate, ethyl acrylate, propyl acrylate, iso-butyl acrylate, sec-butyl acrylate, tert-butyl acrylate, n-pentyl acrylate, iso-amyl acrylate, n-hexyl acrylate, n-heptyl acrylate, methyl methacrylate, ethyl methacrylate, propyl methacrylate, iso-butyl methacrylate, sec-butyl methacrylate, tert-butyl methacrylate, n-pentyl methacrylate, iso-amyl methacrylate, n-hexyl methacrylate, n-heptyl methacrylate, and combinations thereof. More particularly, $C_1$-$C_7$ alkyl (alk)acrylate is selected from the group consisting of methyl acrylate, ethyl acrylate, methyl methacrylate, ethyl methacrylate, and combinations thereof. Even more particularly, $C_1$-$C_7$ alkyl (alk) acrylate is selected from the group consisting of methyl acrylate, methyl methacrylate, and combinations thereof.

Particular, yet non-limiting examples of $C_1$-$C_7$ alkyl (alk) acrylamides (monomer $B_{X1}$) include methyl acrylamide, ethyl acrylamide, propyl acrylamide, iso-butyl acrylamide, sec-butyl acrylamide, tert-butyl acrylamide, n-pentyl acrylamide, iso-amyl acrylamide, n-hexyl acrylamide, n-heptyl acrylamide, methyl methacrylamide, ethyl methacrylamide, propyl methacrylamide, iso-butyl methacrylamide, sec-butyl methacrylamide, tert-butyl methacrylamide, n-pentyl methacrylamide, iso-amyl methacrylamide, n-hexyl methacrylamide, n-heptyl methacrylamide, and combinations thereof. More particularly, $C_1$-$C_7$ alkyl (alk)acrylamide is selected from the group consisting of methyl acrylamide, ethyl acrylamide, methyl methacrylamide, ethyl methacrylamide, and combinations thereof. Even more particularly, $C_1$-$C_7$ alkyl (alk)acrylamide is selected from the group consisting of methyl acrylamide, methyl methacrylamide, and combinations thereof.

In particular embodiments, $C_8$-$C_{60}$ alkyl (alk)acrylate (monomer $B_{X2}$) is an (alk)acrylate comprising a branched $C_8$-$C_{30}$ alkyl moiety. Particular, yet non-limiting examples of (alk)acrylates comprising a branched $C_8$-$C_{30}$ alkyl moiety include 2-ethylhexyl acrylate, 1,1,3,3-tetramethylbutyl acrylate, 1,1-dimethylhexyl acrylate, 6-methylheptyl acrylate, 7-methyloctyl acrylate, 2-propylheptyl acrylate, 8-methylnonyl acrylate, 9-methyldecyl acrylate, 10-methylundecyl acrylate, 11-methyldodecyl acrylate, 12-methyltridecyl acrylate, 13-methyltetradecyl acrylate, 14-methylpentadecyl acrylate, 15-methylhexadecyl acrylate, 16-methylheptadecyl acrylate, 17-methyloctadecyl acrylate, 2-ethylhexyl methacrylate, 1,1,3,3-tetramethylbutyl methacrylate, 1,1-dimethylhexyl methacrylate, 6-methylheptyl methacrylate, 7-methyloctyl methacrylate, 2-propylheptyl methacrylate, 8-methylnonyl methacrylate, 9-methyldecyl methacrylate, 10-methylundecyl methacrylate, 11-methyldodecyl methacrylate, 12-methyltridecyl methacrylate, 13-methyltetradecyl methacrylate, 14-methylpentadecyl methacrylate, 15-methylhexadecyl methacrylate, 16-methylheptadecyl methacrylate, 17-methyloctadecyl methacrylate, and combinations thereof.

In particular embodiments, $C_8$-$C_{60}$ alkyl (alk)acrylamide (monomer $B_{X2}$) is an (alk)acrylamide comprising a branched $C_8$-$C_{30}$ alkyl moiety. Particular, yet non-limiting examples of (alk)acrylamides comprising a branched $C_8$-$C_{30}$ alkyl moiety include N-2-ethylhexyl acrylamide, N-1,1,3,3-tetramethylbutyl acrylamide, N-1,1-dimethylhexyl acrylamide, N-6-methylheptyl acrylamide, N-7-methyloctyl acrylamide, N-2-propylheptyl acrylamide, N-8-methylnonyl acrylamide, N-9-methyldecyl acrylamide, N-10-methylundecyl acrylamide, N-11-methyldodecyl acrylamide, N-12-methyltridecyl acrylamide, N-13-methyltetradecyl acrylamide, N-14-methylpentadecyl acrylamide, N-15-methylhexadecyl acrylamide, N-16-methylheptadecyl acrylamide, N-17-methyloctadecyl acrylamide, N-2-ethylhexyl methacrylamide, N-1,1,3,3-tetramethylbutyl methacrylamide, N-1,1-dimethylhexyl methacrylamide, N-6-methylheptyl methacrylamide, N-7-methyloctyl methacrylamide, N-2-propylheptyl methacrylamide, N-8-methylnonyl methacrylamide, N-9-methyldecyl methacryl-amide, N-10-methylundecyl methacrylamide, N-11-methyldodecyl methacrylamide, N-12-methyltridecyl methacrylamide, N-13-methyltetradecyl methacrylamide, N-14-methylpentadecyl methacrylamide, N-15-methylhexadecyl methacrylamide, N-16-methylheptadecyl methacrylamide, N-17-methyloctadecyl methacrylamide, and combinations thereof.

In a particular embodiment, the polymer that is a component of non-aqueous film forming compositions according to the invention comprises repeating units derived from at least: (a) from about 10 to about 40 percent by weight of the polymer of at least one monomer having a structure selected from the group consisting of:

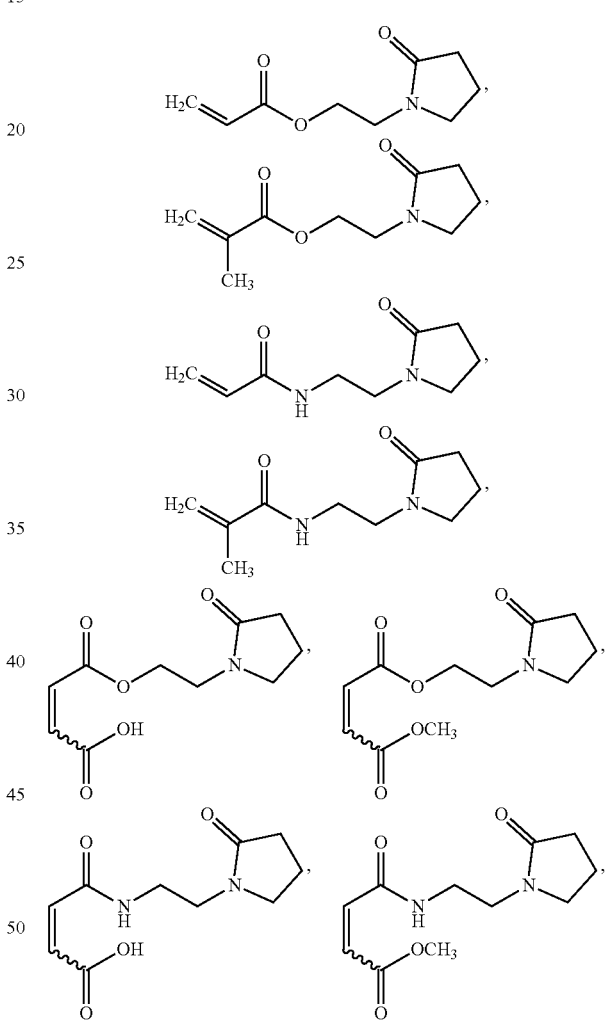

and combinations thereof; (b) from about 15 to about 45 percent by weight of the polymer of at least one monomer selected from the group consisting of methyl acrylate, methyl methacrylate, methyl acrylamide, methyl methacrylamide, and combinations thereof; and (c) from about 25 to about 75 percent by weight of the polymer of at least one monomer selected from the group consisting of 2-ethylhexyl acrylate, 2-ethylhexyl methacrylate, N-2-ethylhexyl acrylamide, N-2-ethylhexyl methacrylamide, and combinations thereof.

More particularly, the film forming polymer comprises repeating units derived from at least: (a) from about 15 to about 25 percent by weight of the polymer of at least one monomer having a structure selected from the group consisting of:

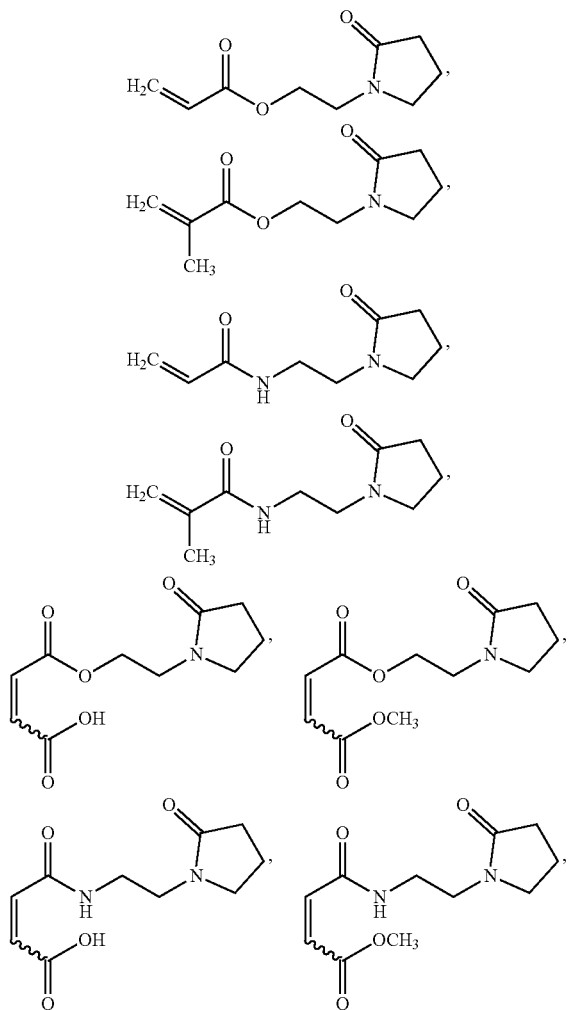

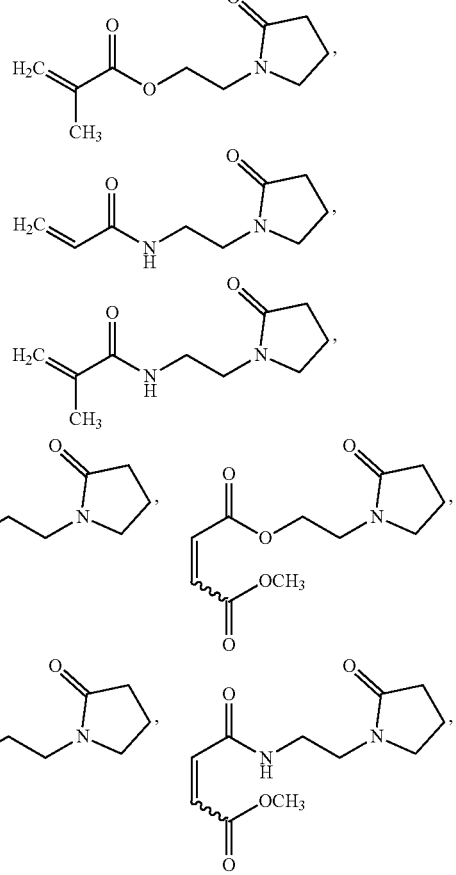

and combinations thereof; (b) from about 20 to about 40 percent by weight of the polymer of at least one monomer selected from the group consisting of methyl acrylate, methyl methacrylate, methyl acrylamide, methyl methacrylamide, and combinations thereof; and (c) from about 40 to about 60 percent by weight of the polymer of at least one monomer selected from the group consisting of 2-ethylhexyl acrylate, 2-ethylhexyl methacrylate, N-2-ethylhexyl acrylamide, N-2-ethylhexyl methacrylamide, and combinations thereof.

Even more particularly, the film forming polymer comprises repeating units derived from at least: (a) about 20 percent by weight of the polymer of at least one monomer having a structure selected from the group consisting of:

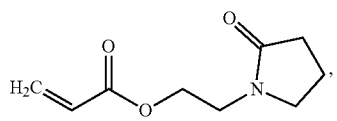

and combinations thereof; (b) about 30 percent by weight of the polymer of at least one monomer selected from the group consisting of methyl acrylate, methyl methacrylate, methyl acrylamide, methyl methacrylamide, and combinations thereof; and (c) about 50 percent by weight of the polymer of at least one monomer selected from the group consisting of 2-ethylhexyl acrylate, 2-ethylhexyl methacrylate, N-2-ethylhexyl acrylamide, N-2-ethylhexyl methacrylamide, and combinations thereof.

Most particularly, the film forming polymer comprises repeating units derived from at least: (a) about 20 percent by weight of the polymer of at least one monomer (monomer A) having a structure selected from the group consisting of:

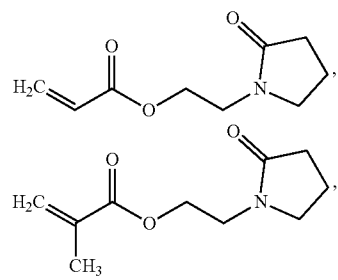

and combinations thereof; (b) about 30 percent by weight of the polymer of at least one monomer (monomer $B_{X1}$) selected from the group consisting of methyl acrylate, methyl methacrylate and combinations thereof; and (c)

about 50 percent by weight of the polymer of at least one monomer (monomer $B_{x2}$) selected from the group consisting of 2-ethylhexyl acrylate, 2-ethylhexyl methacrylate and combinations thereof.

In particular embodiments, the film forming polymer (inventive polymer) that is a component of non-aqueous compositions according to the invention has a structure selected from the group consisting of:

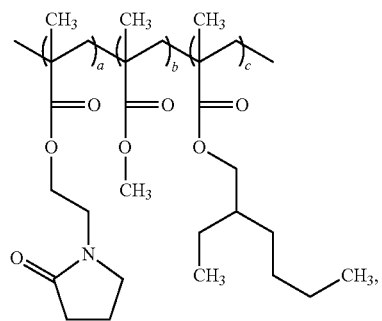

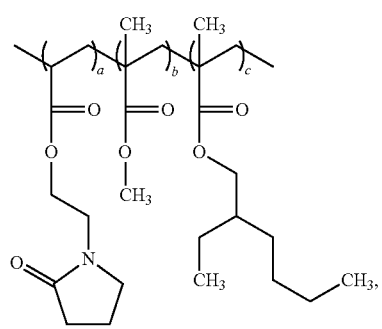

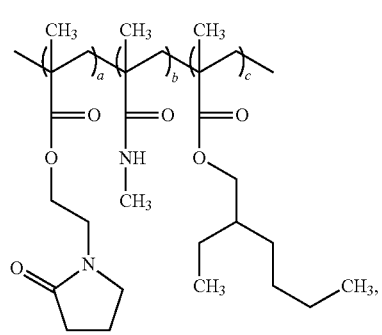

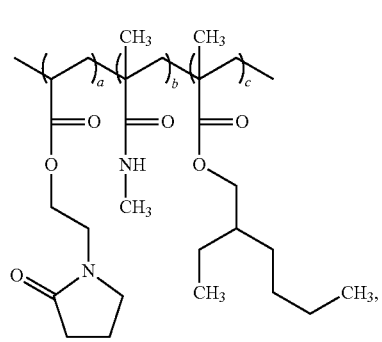

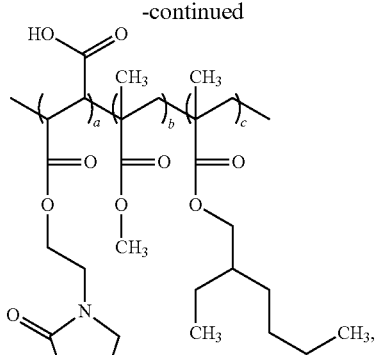

-continued

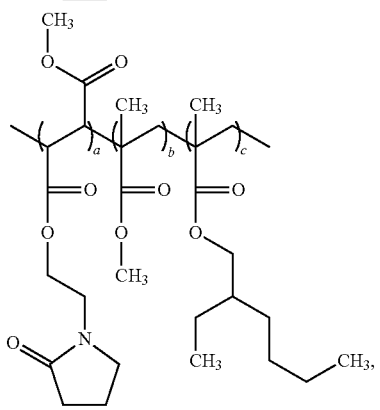

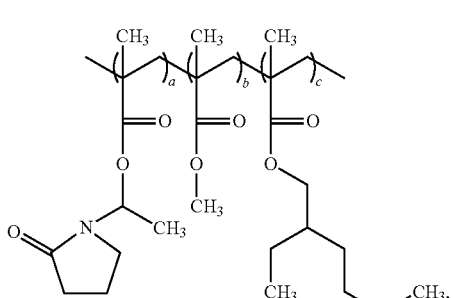

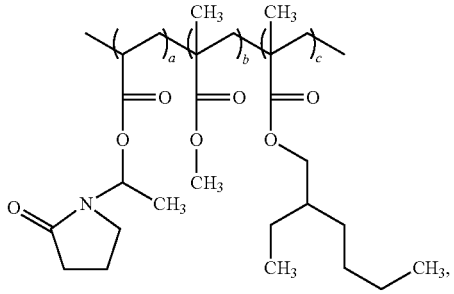

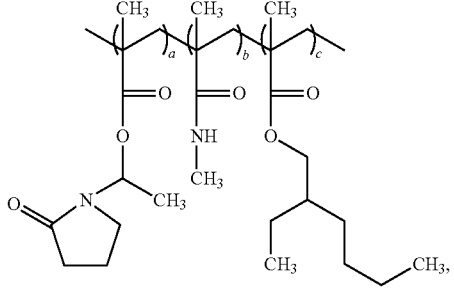

-continued
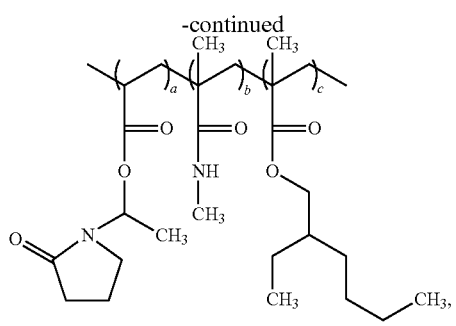
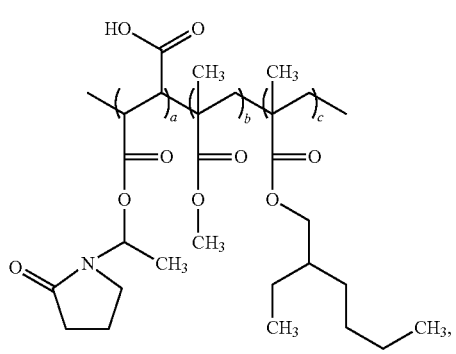
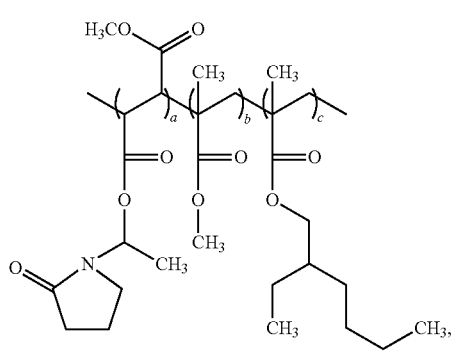
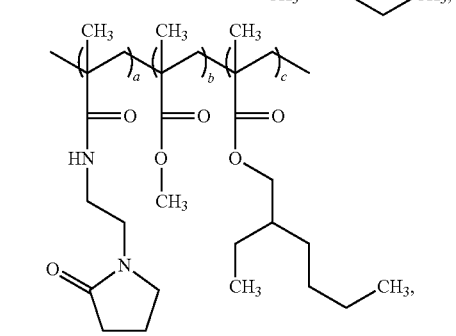
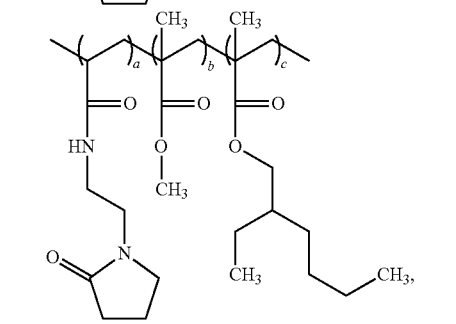
-continued
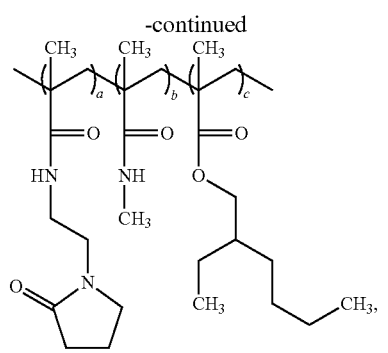
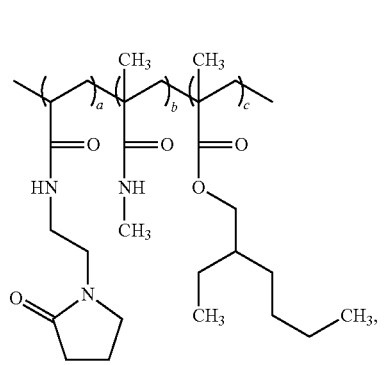
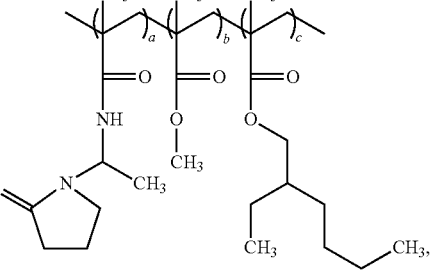
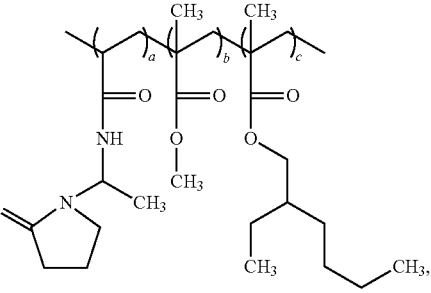
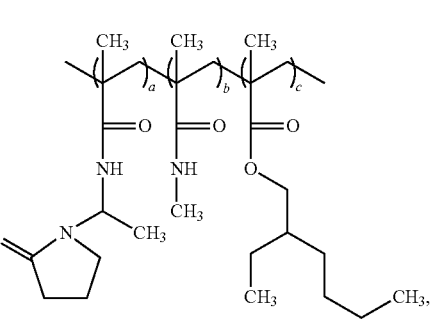

-continued

-continued
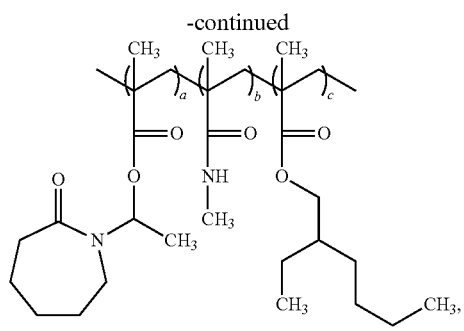
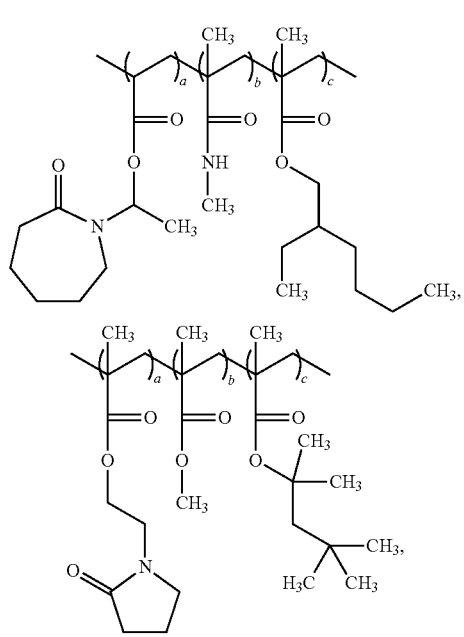
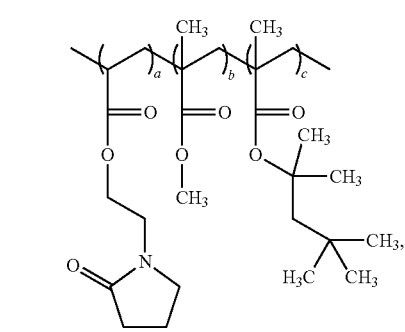
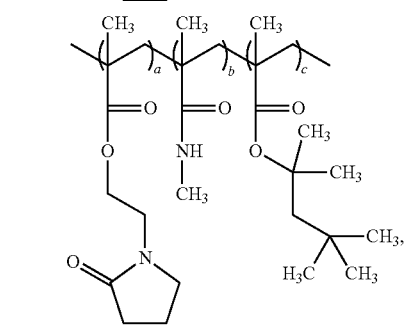
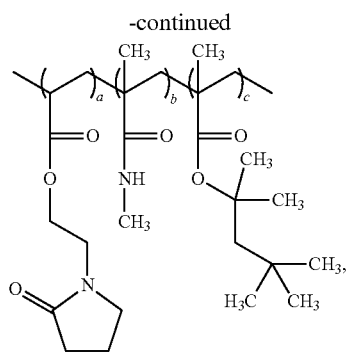
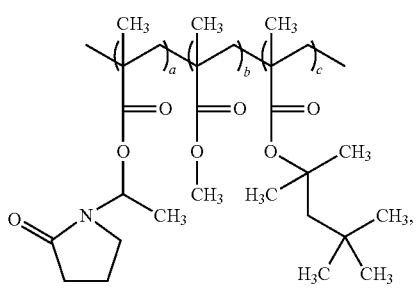
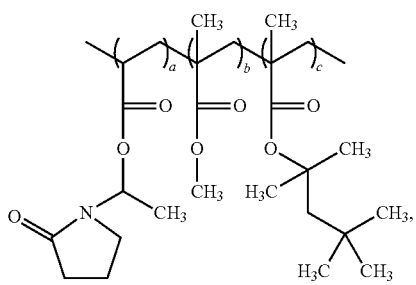
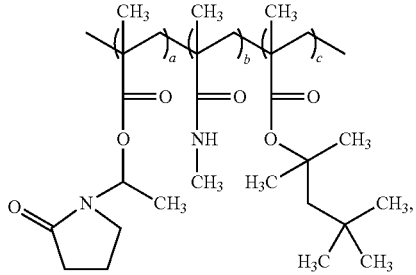
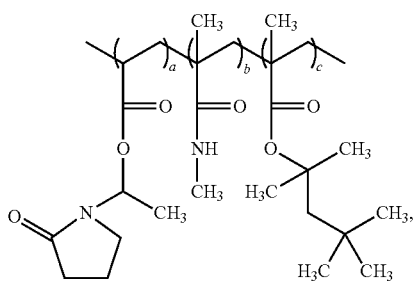

-continued
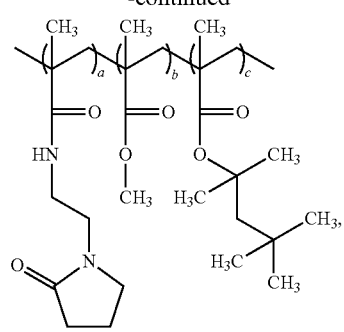
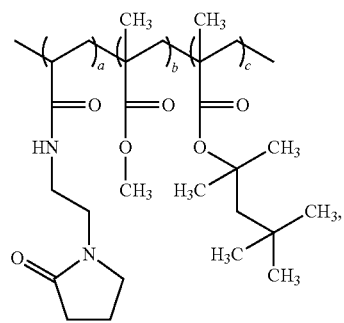
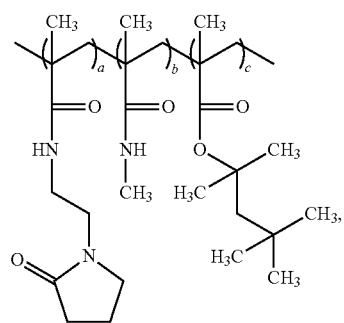
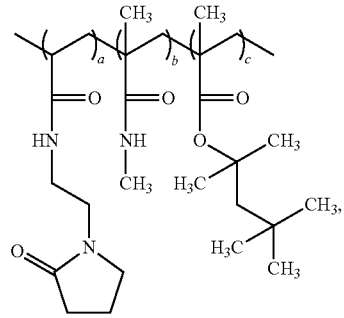
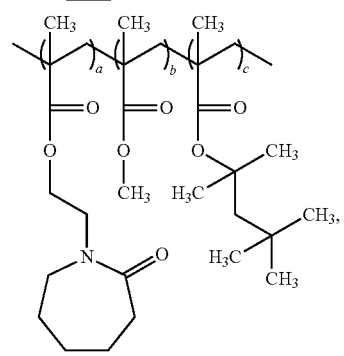
-continued
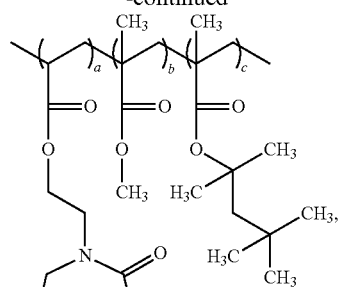
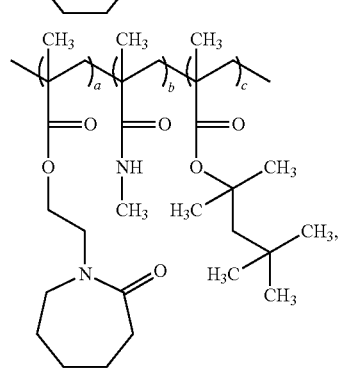
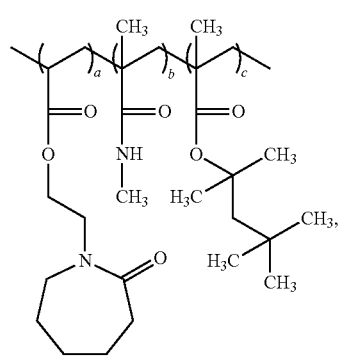
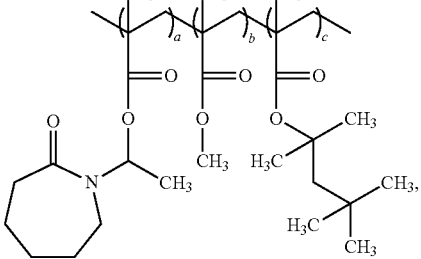
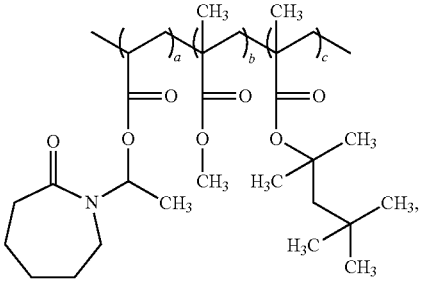

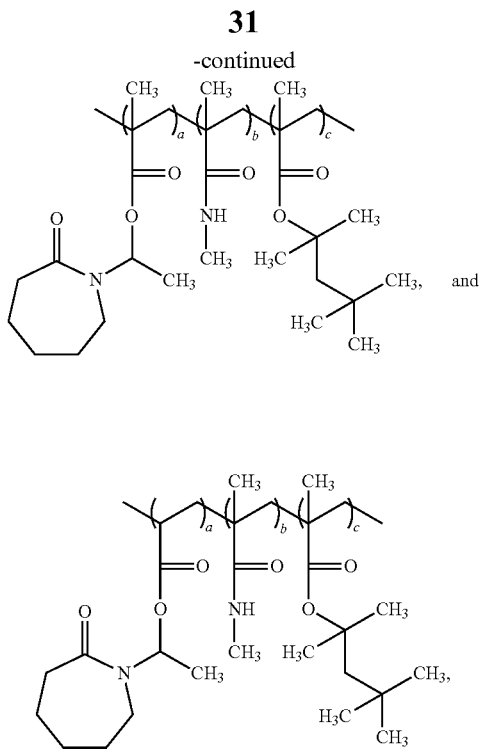

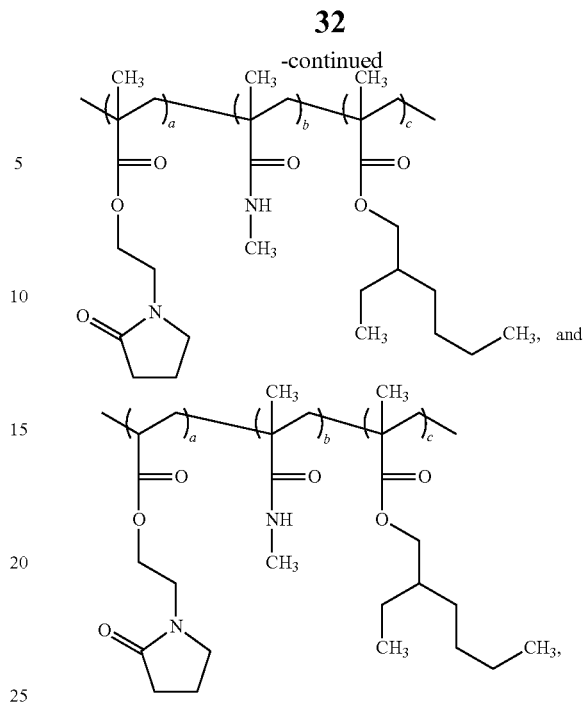

wherein each a, b and c is an independently selected value ranging from about 0.1 to about 99.9 percent by weight of the polymer, with the proviso that the sum of a, b and c for each polymer equals 100 weight percent.

More particularly, the film forming polymer (inventive polymer) that is a component of non-aqueous compositions according to the invention has a structure selected from the group consisting of:

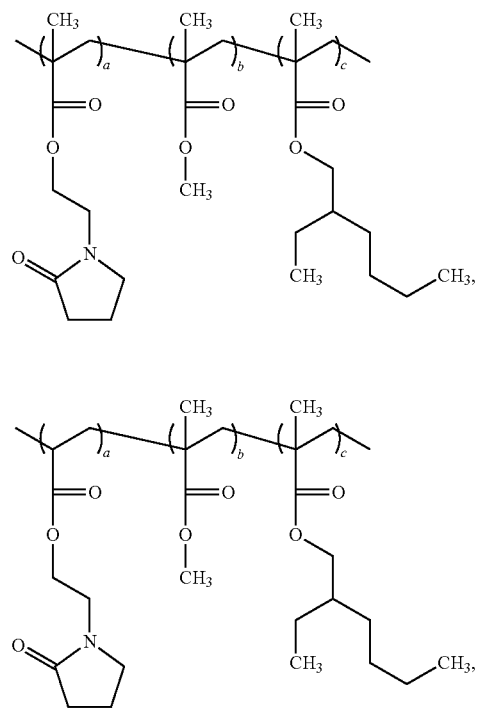

wherein each a, b and c is an independently selected value ranging from about 0.1 to about 99.9 percent by weight of the polymer, with the proviso that the sum of a, b and c for each polymer equals 100 weight percent.

In particular embodiments, the film forming polymer (inventive polymer) that is a component of non-aqueous compositions according to the invention further comprises repeating units derived from at least one monomer selected from the group consisting of functionalized and unfunctionalized N-vinyl lactams, N-vinyl-2-pyrrolidone, N-vinylcaprolactam, alkyl vinyl ethers, methyl vinyl ether, isobutyl vinyl ether, vinyl alkanoates, vinyl acetate, vinyl alkanamides, vinyl alcohols, vinyl carbonates, vinyl carbamates, vinyl thiocarbamates, vinyl ureas, vinyl halides, vinyl imidazoles, vinyl pyridines, vinyl silanes, vinyl siloxanes, vinyl sulfones, maleic anhydride, maleates, fumarates, maleimides, maleamic acids, alpha-olefins, isobutylene, vinyl triazoles, alpha, beta-olefinically unsaturated carboxylic nitriles, acrylonitrile, styrenes, and combinations thereof.

In a particular embodiment, the film forming polymer (inventive polymer) that is a component of non-aqueous compositions according to the invention further comprises repeating units derived from at least one crosslinker.

Non limiting examples of crosslinkers include: divinyl ethers of compounds selected from the group consisting of ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-unidecanediol, 1,12-dodecanediol, and combinations thereof; divinyl ethers of diethylene glycol, triethylene glycol, tetraethylene glycol, pentaethylene glycol, hexaethylene glycol, heptaethylene glycol, octaethylene glycol, nonaethylene glycol, decaethylene glycol, and polyalkylene glycols; methylenebis(meth)acrylamide; ethylene glycol di(meth)acrylate; butanediol di(meth)acrylate; tetraethylene glycol di(meth)acrylate; polyethylene glycol di(meth)acrylate; dipropylene glycol diallyl ether; polyglycol diallyl ether; hydroquinone diallyl ether; trimethylolpropane tri(meth)acrylate; trimethylolpropane diallyl ether; pentaerythritol triallyl ether; allyl(meth)acrylate; triallyl cyanurate; diallyl maleate; polyallyl esters;

tetraallyloxyethane; triallylamine; tetraallylethylenediamine; divinyl benzene; glycidyl (meth)acrylate; 1,7-octadiene; 1,9-decadiene; 1,13-tetradecadiene; divinylbenzene; diallyl phthalate; triallyl-1,3,5-triazine-2,4,6(1H,3H,5H)-trione; N,N'-divinylimidazolidone; 1-vinyl-3(E)-ethylidene pyrrolidone; 2,4,6-triallyloxy-1,3,5-triazine; and combinations thereof.

Particularly, the crosslinker(s) may be present in an amount from about 0.001% by weight to about 20% by weight of the polymer. More particularly, the crosslinker(s) may be present in an amount from about 0.001% by weight to about 10% by weight of the polymer. Even more particularly, the crosslinker(s) may be present in an amount from about 0.001% by weight to about 5% by weight of the polymer.

The non-aqueous compositions according to the invention may be used as such or formulated with other ingredient(s) resulting in various product forms.

In particular embodiments, the non-aqueous composition according to the invention is a personal care composition, cementing fluid, oilfield composition, construction composition, servicing fluid, gravel packing mud, fracturing fluid, completion fluid, workover fluid, spacer fluid, drilling mud, coating composition, household, industrial and institutional composition, pharmaceutical composition, food composition, biocide, adhesive, ink, paper, polish, membrane, metal working fluid, plastic, textile, printing composition, lubricant, preservative, agrochemical, or wood-care composition. Particularly, the non-aqueous composition is a personal care composition, coating composition, household, industrial and institutional composition, pharmaceutical composition, or an agricultural composition. More particularly, the non-aqueous composition is a personal care composition.

In a second aspect, the invention provides a non-aqueous personal care composition comprising a film forming polymer (inventive polymer) comprising repeating units derived from at least: (a) at least one monomer comprising at least one functionalized or unfunctionalized acryloyl moiety and at least one lactam moiety; (b) at least one monomer selected from the group consisting of functionalized and unfunctionalized $C_1$-$C_7$ alkyl (alk)acrylates, $C_1$-$C_7$ alkyl (alk)acrylamides, and combinations thereof; and (c) at least one monomer selected from the group consisting of functionalized and unfunctionalized $C_8$-$C_{60}$ alkyl (alk)acrylates, $C_8$-$C_{60}$ alkyl (alk)acrylamides, and combinations thereof.

Particular, yet non-limiting examples of non-aqueous personal care compositions include sun care compositions, face care compositions, lip care compositions, eye care compositions, skin care compositions, after-sun compositions, body care compositions, nail care compositions, anti-aging compositions, insect repellants, oral care compositions, deodorant compostions, hair care compositions, conditioning compositions, color cosmetic compositions, color-protection compositions, self-tanning compositions, and foot care compositions.

In particular embodiments, the non-aqueous personal care compositions according to the invention further comprise at least one pharmaceutically- or cosmetically-acceptable organic liquid. Particular, yet non-limiting examples of organic liquids include oils, waxes, triglycerides, fatty esters, fatty amides, fatty hydrocarbons, and combinations thereof. More particularly, the organic liquid may be selected from the group consisting of saturated fatty esters and diesters, isopropyl palmitate, octyl palmitate, butyl stearate, isocetyl stearate, octadecyl stearoyl stearate, diisopropyl adipate, dioctyl sebacate, paraffin oils, paraffin waxes, animal oils, vegetable oils, mink oil, coconut oil, soybean oil, palm oil, corn oil, cocoa butter, sesame oil, lanolin oil, fatty alcohols, stearyl alcohol, isostearyl alcohol, isocetyl alcohol, and combinations thereof. Even more particularly, the organic liquid is at least one Ceraphyl™ ester available for sale from Ashland Inc.

In a particular embodiment, the non-aqueous personal care composition according to the invention is a composition for providing water resistance to a keratinous substrate. Particularly, the composition is a sun care composition for providing water resistance to a keratinous substrate.

In particular embodiments, the non-aqueous personal care compositions according to the invention may further comprise at least one additive selected from the group consisting of secondary polymers for improving water-resistance, UV actives, UV active solubilizers, oils, waxes, solvents, emulsifiers, preservatives, antioxidants, antiradical protecting agents, vitamins, perfumes, insect repellants, dyes, pigments, humectants, fillers, thickeners, film formers, stabilizers, buffers, spreading agents, pearlizing agents, electrolytes, acids, bases, crystalline structuring agents, abrasives, pharmaceutically or cosmetically acceptable excipients, and combinations thereof.

In particular embodiments, the non-aqueous personal care composition according to the invention is in the form of an oil dispersion, oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous formulation, an anhydrous gel, an alcoholic solution, or a hydro-alcoholic solution. More particularly, the non-aqueous personal care composition according to the invention is in the form of an oil dispersion.

In particular embodiments, the film forming polymer that is a component of non-aqueous personal care compositions according to the invention is present in an amount from about 0.01% by weight to about 20% by weight of the composition. More particularly, the polymer is present in an amount from about 0.1% by weight to about 10% by weight of the composition. Even more particularly, the polymer is present in an amount from about 0.25% by weight to about 5.0% by weight of the composition.

In a particular embodiment, the non-aqueous personal care composition according to the invention has turbidity less than about 100 NTU. Preferably, less than about 50 NTU.

Being non-aqueous, the compositions according to the invention may be particularly suitable as vehicles for active ingredients which may be physically or chemically incompatible with water, or which may function less efficiently in an aqueous environment.

Methods of Synthesis

The film forming polymers that are components of non-aqueous compositions according to the invention may be readily synthesized by procedures known by those skilled in the art, non-limiting examples of which include free radical solution polymerization, dispersion polymerization, emulsion polymerization, ionic chain polymerization, living polymerization, and precipitation polymerization.

Free radical polymerization may be used, especially when using water-dispersible and/or water-soluble reaction solvent(s). This type of polymerization method is described in "Decomposition Rate of Organic Free Radical Polymerization" by K. W. Dixon (section II in Polymer Handbook, volume 1, 4th edition, Wiley-Interscience, 1999), which is herein incorporated in its entirety by reference.

Compounds capable of initiating the free-radical polymerization include those materials known to function in the prescribed manner, and include the peroxo and azo classes of materials. Peroxo and azo compounds include, but are not limited to: acetyl peroxide; azo bis-(2-amidinopropane) dihydrochloride; azo bis-isobutyronitrile; 2,2'-azo bis-(2-methylbutyronitrile); benzoyl peroxide; di-tert-amyl peroxide; di-tert-butyl diperphthalate; butyl peroctoate; tert-butyl dicumyl peroxide; tert-butyl hydroperoxide; tert-butyl perbenzoate; tert-butyl permaleate; tert-butyl perisobutylrate; tert-butyl peracetate; tert-butyl perpivalate; para-chlorobenzoyl peroxide; cumene hydroperoxide; diacetyl peroxide; dibenzoyl peroxide; dicumyl peroxide; didecanoyl peroxide; dilauroyl peroxide; diisopropyl peroxodicarbamate; dioctanoyl peroxide; lauroyl peroxide; octanoyl peroxide; succinyl peroxide; and bis-(ortho-toluoyl) peroxide. Also suitable to initiate the free-radical polymerization are initiator mixtures or redox initiator systems, including: ascorbic acid/iron (II) sulfate/sodium peroxodisulfate, tert-butyl hydroperoxide/sodium disulfite, and tert-butyl hydroperoxide/sodium hydroxymethanesulfinate.

The polymerization reactions may be carried out in the presence of one or more solvents. Non-limiting examples of solvents that may be employed include ethanol, isopropanol, tert-butanol, n-hexane, and Ceraphyl® 230. The polymers may be synthesized in a solvent or a blend of one or more solvents and maintained therein, or the synthesis solvent(s) separated from the polymer by methods known in the art and replaced by a solvent beneficial for formulary development and/or end-use. The polymerization temperature may vary from about 5° C. to about 200° C. The polymerization reaction may be carried out at ambient pressure, sub-atmospheric pressure, or super-atmospheric pressure. The polymerization reaction may be carried out in a batch, continuous and/or semi-continuous manner.

In particular embodiments, the non-crosslinked polymers that are components of non-aqueous compositions according to the invention may have a weight-average molecular weight ranging from about 10,000 Da to about 1,000,000 Da, more particularly from about 25,000 Da to about 500,000 Da, and even more particularly from about 50,000 Da to about 250,000 Da. There is no restriction on molecular weights for crosslinked polymers.

The molecular weight may be controlled using methods known in the art, including strategies to control the reaction temperature and time, as well as the use of chain-transfer agents such as thiols (e.g., dodecyl mercaptan), and halo-carbons (e.g., chlorinated compounds like carbon tetrachloride)

Characterization of Polymers

The film forming polymers and compositions comprising the film forming polymers according to the invention may be analyzed by known techniques. Especially preferred are the techniques of $^{13}C$ nuclear magnetic resonance (NMR) spectroscopy, gas chromatography (GC), and gel permeation chromatography (GPC) in order to decipher polymer identity, residual monomer concentrations, polymer molecular weight, and polymer molecular weight distribution.

Nuclear magnetic resonance (NMR) spectroscopy is an especially preferred method to probe the polymerization product in terms of chemical properties such as monomeric composition, sequencing and tacticity. Analytical equipment suitable for these analyses includes the Inova 400-MR NMR System by Varian Inc. (Palo Alto, Calif.). References broadly describing NMR include: Yoder, C. H. and Schaeffer Jr., C. D., *Introduction to Multinuclear NMR*, The Benjamin/Cummings Publishing Company, Inc., 1987; and Silverstein, R. M., et al., *Spectrometric Identification of Organic Compounds*, John Wiley & Sons, 1981, which are incorporated in their entirety by reference.

Residual monomer levels can be measured by GC, which can be used to indicate the extent of reactant conversion by the polymerization process. GC analytical equipment to perform these tests are commercially available, and include the following units: Series 5880, 5890, and 6890 GC-FID and GC-TCD by Agilent Technologies, Inc. (Santa Clara, Calif.). GC principles are described in *Modern Practice of Gas Chromatography*, third edition (John Wiley & Sons, 1995) by Robert L. Grob and Eugene F. Barry, which is hereby incorporated in its entirety by reference.

GPC is an analytical method that separates molecules based on their hydrodynamic volume (or size) in solution of the mobile phase, such as hydroalcoholic solutions with surfactants. GPC is a preferred method for measuring polymer molecular weight distributions. This technique can be performed on known analytical equipment sold for this purpose, and include the TDAmax™ Elevated Temperature GPC System and the RImax™ Conventional Calibration System by Viscotek™ Corp. (Houston, Tex.). In addition, GPC employs analytical standards as a reference, of which a plurality of narrow-distribution polyethylene glycol and polyethylene oxide standards representing a wide range in molecular weight is the preferred. These analytical standards are available for purchase from Rohm & Haas Company (Philadelphia, Pa.) and Varian Inc. (Palo Alto, Calif.). GPC is described in the following texts, which are hereby incorporated in their entirety by reference: Schroder, E., et al., *Polymer Characterization*, Hanser Publishers, 1989; Billingham, N.C., *Molar Mass Measurements in Polymer Science*, Halsted Press, 1979; and Billmeyer, F., *Textbook of Polymer Science*, Wiley Interscience, 1984.

The film forming polymers that are components of non-aqueous compositions according to the invention may be prepared according to the procedures set out below. The examples are presented for purposes of demonstrating, but not limiting, the preparation of the polymers. Therein, the following abbreviations are used:

UV: Ultra violet
PyEMA: Pyrrolidonylethyl methacrylate
EHMA: 2-ethylhexyl methacrylate
MMA: Methyl methacrylate
TBA: tert-butyl acrylate

EXAMPLES

Example 1: Synthesis of Poly(PyEMA-co-MMA-co-EHMA) with PyEMA/MMA/EHMA Weight Ratio of 20:30:50

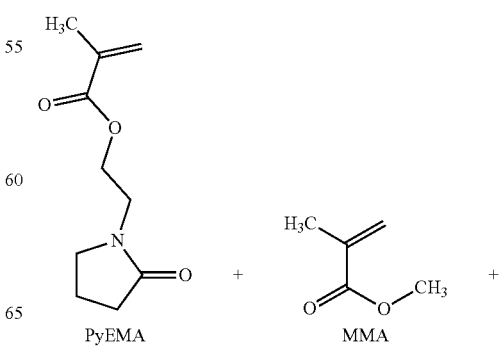

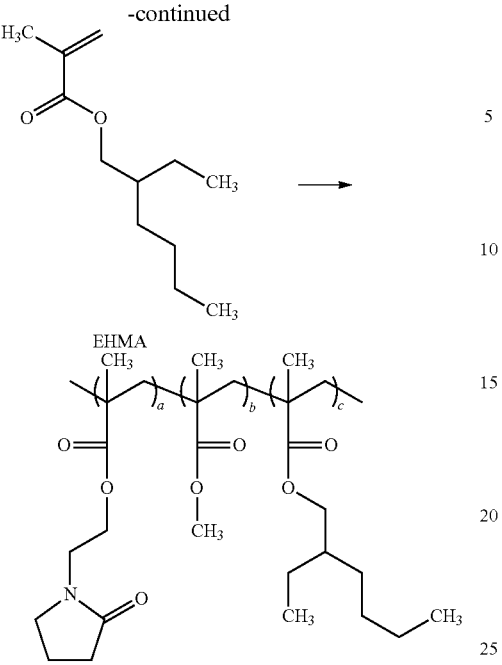

An amount of 30 g of PyEMA, 75 g of EHMA and 45 g of MMA was premixed into 350 g tert-butanol and stirred for 10 minutes. 10% of this solution (50 g) was placed into a reactor as a heel charge and sparged with nitrogen gas for 5 minutes. The reactor containing heel was heated to 68° C. and then initiated with 0.3% Trigonox® 25-C75. The feed containing 450 g of monomer charge was then added over 4 hours. Every 1.5 hours after first initiation, a booster charge of 0.15% Trigonox® 25-C75 was added for a total of 3 shots of initiator over the total feed charge. After monomer addition was completed, residual monomers were chased down with 0.3 g Trigonox® 121 every hour for three more hours at 85° C. The reaction mixture was held at 85° C. for 1 hour and then cooled to 25° C. and discharged as a clear viscous product. Residual monomers were <1000 ppm. In the polymer structure shown, a=20 weight %, b=30 weight % and c=50 weight %.

Example 2: Synthesis of Poly(PyEMA-co-MMA-co-EHMA) with PyEMA/MMA/EHMA Weight Ratio of 20:30:50. Four Hour Feed Reaction in Tert-Butanol Solvent

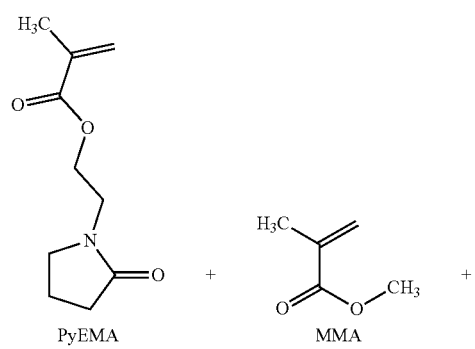

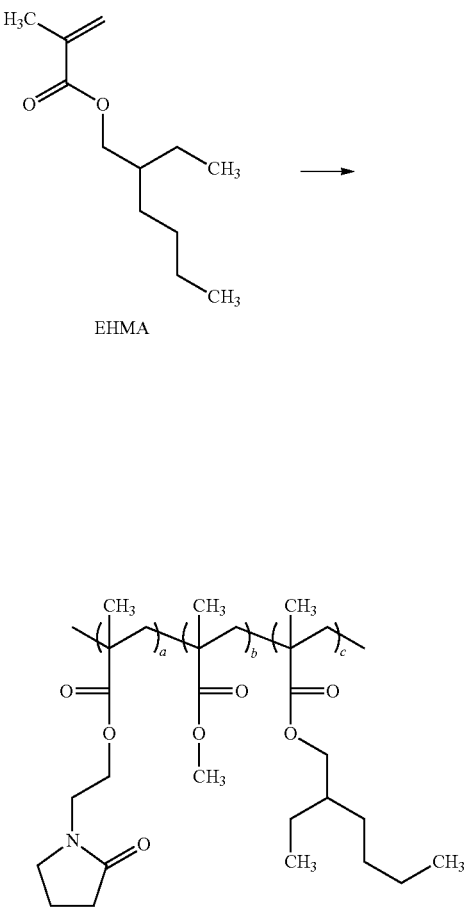

An amount of 36 g of PyEMA and 75 g tert-butanol is added to the reaction vessel as a heel charge. The reaction mixture is purged three times with nitrogen while stirring and then heated to 75° C. to 85° C. A pre-mixed feed charge comprising 90 g of EHMA, 54 g of MMA, and tert-butanol is fed in the pump. The feed is started at 70° C. to 80° C. and continued for four hours. The jacket temperature is adjusted to maintain the internal temperature between 80 to 85° C. during the feed. A total amount of 0.9 g of the initial initiator Luperox® 11 is charged in six portions during the feed. After the feed is completed, tert-butanol is used to rinse the feeding line, pump and charge line, and discharged into the reaction vessel. The reaction mixture is maintained on hold for one hour at 80° C. to 85° C. An amount of 2.0% by weight of total amount of monomers of chaser initiator Luperox® 11 is charged in 12 portions and the reaction sampled for analysis by HPLC. The mixture is maintained on hold for 10 hours at 80° C. to 85° C. The sample is dried under high vacuum at 50° C. to 55° C. In the polymer structure shown, a=20 weight %, b=30 weight % and c=50 weight %.

Example 3: Synthesis of Poly(PyEMA-co-MMA-co-EHMA) with PyEMA/MMA/EHMA Weight Ratio of 20:30:50. Two Hour Feed Reaction in Tert-Butanol Solvent

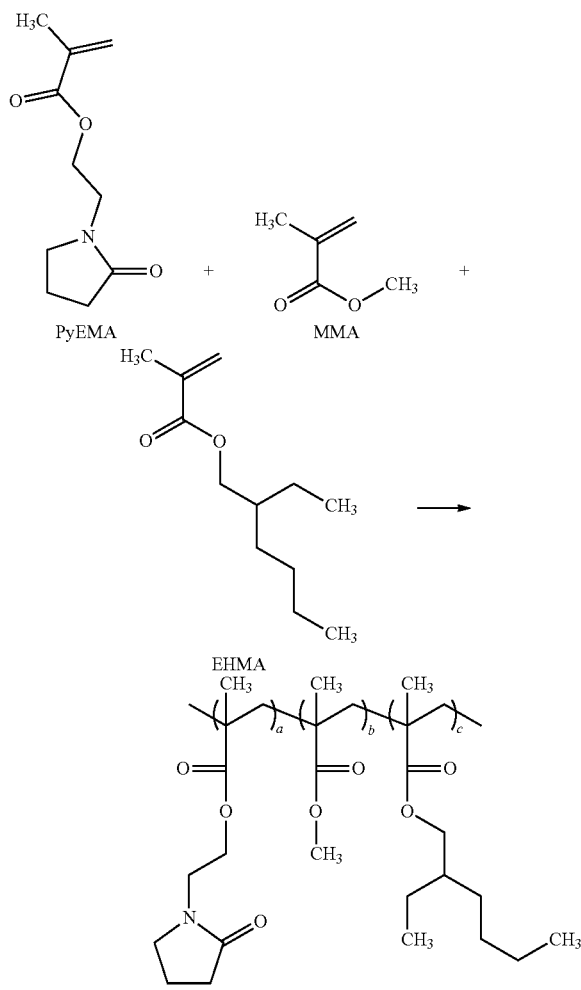

An amount of 36 g of PyEMA and 75 g tert-butanol is added to the reaction vessel as a heel charge. The reaction mixture is purged three times with nitrogen while stirring and then heated to 80° C. to 85° C. A pre-mixed feed charge comprising 90 g of EHMA, 54 g of MMA, and 150 g of tert-butanol is fed in the pump. The feed is started at 70° C. to 80° C. and continued for two hours. The jacket temperature is adjusted to maintain the internal temperature between 80 to 85° C. during the feed. A total amount of 0.9 g of the initial initiator Vazo® 67 is charged in two portions during the feed. After the feed is completed, tert-butanol is used to rinse the feeding line, pump and charge line, and discharged into the reaction vessel. The reaction mixture is maintained on hold for one hour at 80° C. to 85° C. An amount of 2.0% by weight of total amount of monomers of chaser initiator Luperox® 121 is charged after every hour after the temperature increased to 90° C. to 91° C. and the reaction sampled for analysis by HPLC. The mixture is maintained on hold for 10 hours at 90° C. to 95° C. The sample is dried under high vacuum at 50° C. to 55° C. In the polymer structure shown, a=20 weight %, b=30 weight % and c=50 weight %.

Example 4: Synthesis of Poly(PyEMA-co-MMA-co-EHMA) with PyEMA/MMA/EHMA Weight Ratio of 20:30:50. One Hour Feed Reaction in Tert-Butanol Solvent

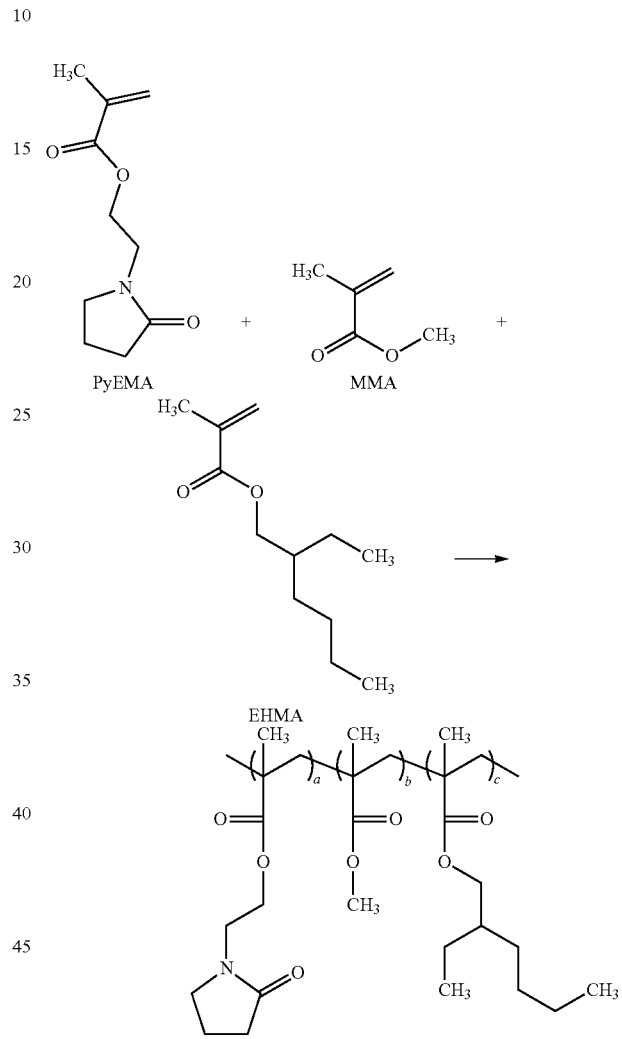

An amount of 36 g of PyEMA and 75 g tert-butanol is added to the reaction vessel as a heel charge. The reaction mixture is purged three times with nitrogen while stirring and then heated to 70° C. to 75° C. A pre-mixed feed charge comprising 90 g of EHMA, 54 g of MMA, and tert-butanol is fed in the pump. The feed is started at 70° C. to 75° C. and continued for one hour. The jacket temperature is adjusted to maintain the internal temperature between 70 to 75° C. during the feed. A total amount of 0.9 g of the initial initiator Luperox® 11 is charged in one portion during the feed. After the feed is completed, tert-butanol is used to rinse the feeding line, pump and charge line, and discharged into the reaction vessel. The reaction mixture is maintained on hold for one hour at 85° C. to 90° C. An amount of 2.0% by weight of total amount of monomers of chaser initiator Luperox® 121 is charged in four portions after every hour. The reaction mixture is maintained on hold for 10 hours at 85° C. to 90° C. The sample is dried under high vacuum at 50° C. to 55° C. In the polymer structure shown, a=20 weight %, b=30 weight % and c=50 weight %.

Example 5: Synthesis of Poly(PyEMA-co-MMA-co-EHMA) with PyEMA/MMA/EHMA Weight Ratio of 30:30:40. Three Hour Feed Reaction in Tert-Butanol Solvent

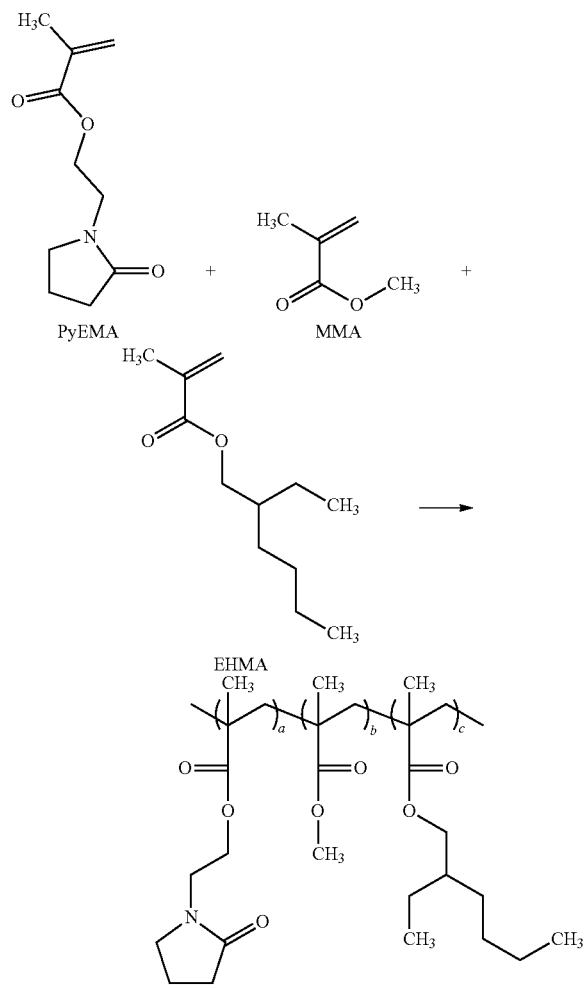

An amount of 54 g of PyEMA and 75 g tert-butanol is added to the reaction vessel as a heel charge. The reaction mixture is purged three times with nitrogen while stirring and then heated to 80° C. to 85° C. A pre-mixed feed charge comprising 72 g of EHMA, 54 g of MMA, and tert-butanol is fed in the pump. The feed is started at 70° C. to 80° C. and continued for three hours. The jacket temperature is adjusted to maintain the internal temperature between 80 to 85° C. during the feed. A total amount of 0.9 g of the initial initiator Vazo® 67 is charged in six portions during the feed. After the feed is completed, tert-butanol is used to rinse the feeding line, pump and charge line, and discharged into the reaction vessel. The reaction mixture is maintained on hold for one hour at 85° C. to 85° C. and sampled for analysis by HPLC. An amount of 2.5% by weight of total amount of monomers of chaser initiator Vazo® 67 is charged in six portions. The reaction mixture is maintained on hold for 10 hours at 80° C. to 85° C. The sample is dried under high vacuum at 50° C. to 55° C. In the polymer structure shown, a=30 weight %, b=30 weight % and c=40 weight %.

Example 6: Synthesis of Poly(PyEMA-co-TBA-co-EHMA) with PyEMA/TBA/EHMA Weight Ratio of 20:30:50. Four Hour Feed Reaction in Tert-Butanol Solvent

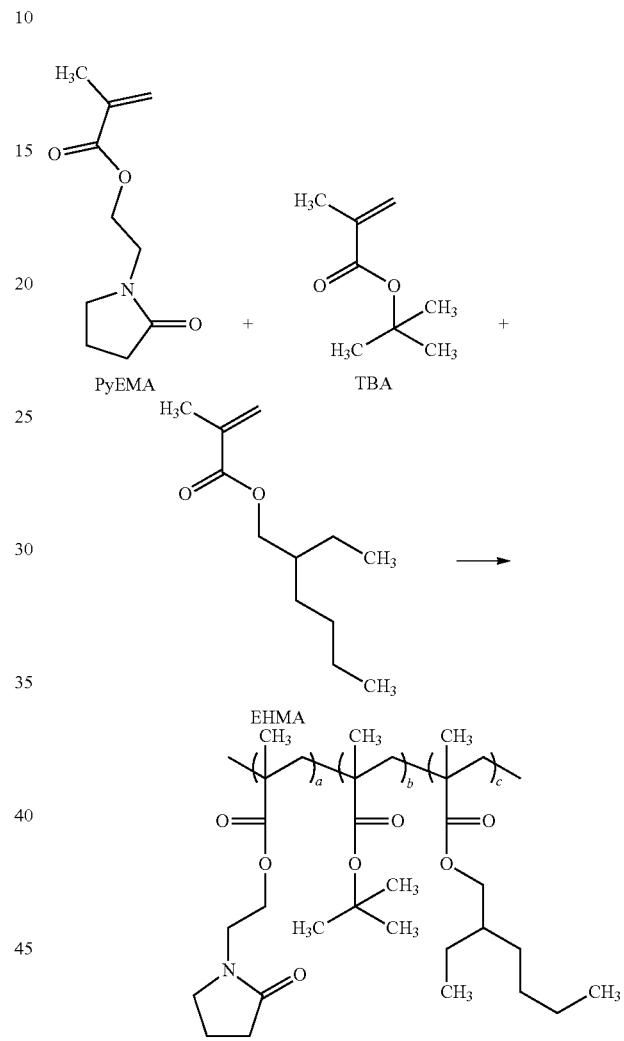

An amount of 36 g of PyEMA and 75 g tert-butanol is added to the reaction vessel as a heel charge. The reaction mixture is purged three times with nitrogen while stirring and then heated to 70° C. to 75° C. A pre-mixed feed charge comprising 90 g of EHMA, 54 g of TBA, and tert-butanol is fed in the pump. The feed is started at 70° C. to 80° C. and continued for four hours. The jacket temperature is adjusted to maintain the internal temperature between 70 to 75° C. during the feed. A total amount of 0.9 g of the initial initiator Luperox® 11 is charged in six portions during the feed. After the feed is completed, tert-butanol is used to rinse the feeding line, pump and charge line, and discharged into the reaction vessel. The reaction mixture is maintained on hold for one hour at 70° C. to 75° C. and sampled for analysis. The temperature is raised to 80° C.-85° C. An amount of 2.5% by weight of total amount of monomers of chaser initiator Luperox® 11 is charged in six portions every hour.

The reaction mixture is maintained on hold for 10 hours at 80° C. to 85° C. and sampled for analysis by HPLC. The sample is dried under high vacuum at 50° C. to 55° C. In the polymer structure shown, a=20 weight %, b=30 weight % and c=50 weight %.

Example 7: Synthesis of Poly(PyEMA-co-MMA-co-EHMA) with PyEMA/MMA/EHMA Weight Ratio of 20:30:50. Four Hour Feed Reaction in Isopropanol Solvent

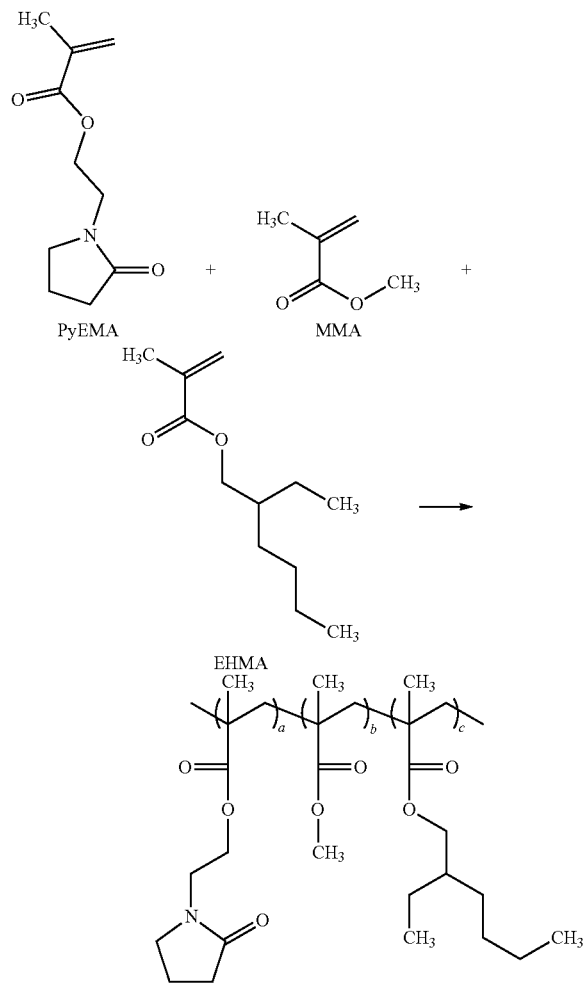

An amount of 36 g of PyEMA and 75 g tert-butanol is added to the reaction vessel as a heel charge. The reaction mixture is purged three times with nitrogen while stirring and then heated to 70° C. to 80° C. A pre-mixed feed charge comprising 90 g of EHMA, 54 g of MMA, tert-butanol and 30 g of isopropanol is fed in the pump. The feed is started at 70° C. to 80° C. and continued for four hours. The jacket temperature is adjusted to maintain the internal temperature between 70 to 75° C. during the feed. A total amount of 1.35 g of the initial initiator Luperox® 11 is charged in six portions during the feed. After the feed is completed, tert-butanol is used to rinse the feeding line, pump and charge line, and discharged into the reaction vessel. The reaction mixture is maintained on hold for one hour at 70° C. to 75° C. and sampled for analysis. The temperature is raised to 80° C.-85° C. An amount of 2.5% by weight of total amount of monomers of chaser initiator Luperox® 11 is charged in six portions every hour. The reaction mixture is maintained on hold for 10 hours at 80° C. to 85° C. and sampled for analysis by HPLC. The sample is dried under high vacuum at 50° C. to 55° C. In the polymer structure shown, a=20 weight %, b=30 weight % and c=50 weight %.

Example 8: Synthesis of Poly(PyEMA-co-MMA-co-EHMA) with PyEMA/MMA/EHMA Weight Ratio of 20:50:30. Three Hour Feed Reaction in Tert-Butanol Solvent

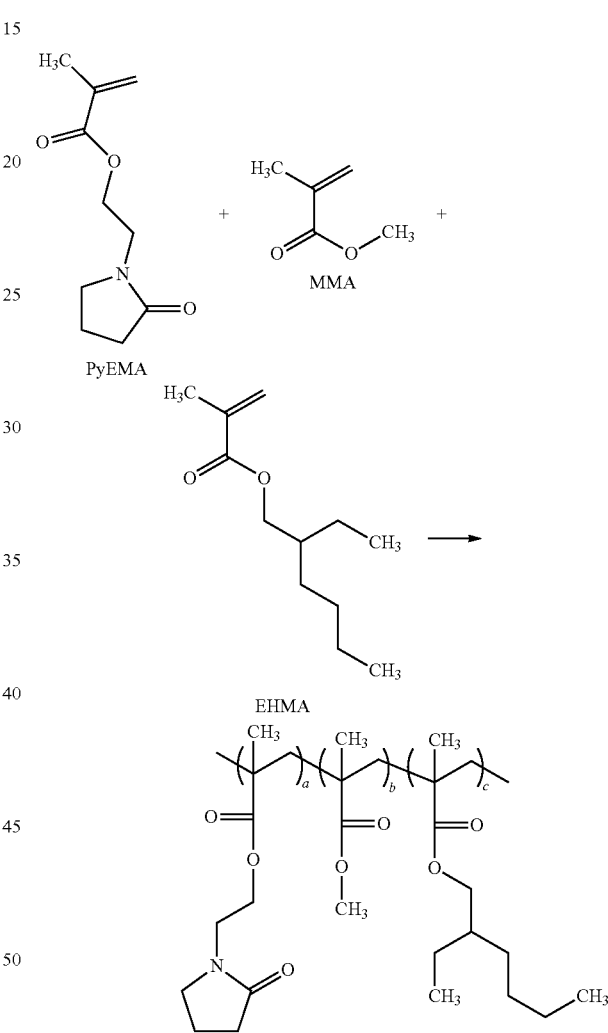

An amount of 36 g of PyEMA and 75 g tert-butanol is added to the reaction vessel as a heel charge. The reaction mixture is purged three times with nitrogen while stirring and then heated to 80° C. to 85° C. A pre-mixed feed charge comprising 54 g of EHMA, 90 g of MMA, and tert-butanol is fed in the pump. The feed is started at 70° C. to 80° C. and continued for three hours. The jacket temperature is adjusted to maintain the internal temperature between 80 to 85° C. during the feed. A total amount of 0.9 g of the initial initiator Luperox® 11 is charged in six portions during the feed. After the feed is completed, tert-butanol is used to rinse the feeding line, pump and charge line, and discharged into the reaction vessel. The reaction mixture is maintained on hold for one hour at 80° C. to 85° C. and sampled for analysis. An amount of 2.5% by weight of total amount of monomers of chaser initiator Luperox® 11 is charged in six portions every hour. The reaction mixture is maintained on hold for 10 hours at 80° C. to 85° C. and sampled for analysis by HPLC. The sample is dried under high vacuum at 50° C. to 55° C. In the polymer structure shown, a=20 weight %, b=50 weight % and c=30 weight %.

Example 9: Synthesis of Poly(PyEMA-co-MMA-co-EHMA) with PyEMA/MMA/EHMA Weight Ratio of 20:30:50. Four Hour Feed Reaction in Isopropanol and Tert-Butanol Solvent Combination (30% Solids Process)

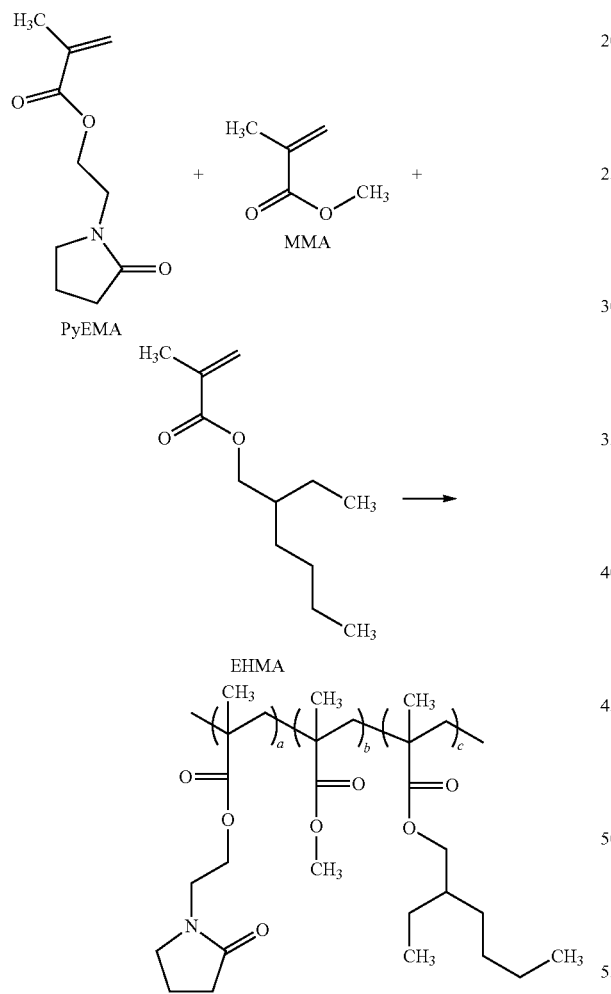

An amount of 36 g of PyEMA and 75 g tert-butanol is added to the reaction vessel as a heel charge. The reaction mixture is purged three times with nitrogen while stirring and then heated to 75° C. to 80° C. A pre-mixed feed charge comprising 90 g of EHMA, 54 g of MMA, tert-butanol and 15 g of isopropanol is fed in the pump. The feed is started at 70° C. and continued for four hours. The jacket temperature is adjusted to maintain the internal temperature between 75 to 80° C. during the feed. A total amount of 1.35 g of the initial initiator Luperox® 11 is charged in six portions during the feed. After the feed is completed, tert-butanol is used to rinse the feeding line, pump and charge line, and discharged into the reaction vessel. The reaction mixture is maintained on hold for one hour at 80° C. to 85° C. and sampled for analysis by HPLC. The temperature is raised to 80° C.-85° C. An amount of 2.5% by weight of total amount of monomers of chaser initiator Luperox® 11 is charged in six portions every hour. The reaction mixture is maintained on hold for 10 hours at 80° C. to 85° C. The sample is dried under high vacuum at 50° C. to 55° C. In the polymer structure shown, a=20 weight %, b=30 weight % and c=50 weight %.

Example 10: Synthesis of Poly(PyEMA-co-MMA-co-EHMA) with PyEMA/MMA/EHMA Weight Ratio of 20:30:50. Four Hour Feed Reaction in Isopropanol and Tert-Butanol Solvent Combination (40% Solids Process)

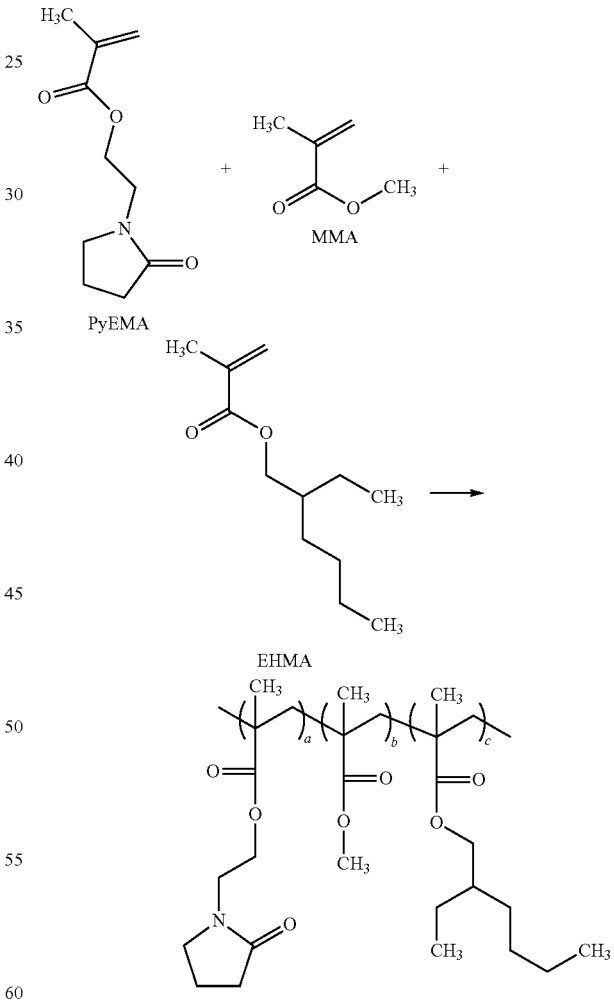

An amount of 36 g of PyEMA and 75 g tert-butanol is added to the reaction vessel as a heel charge. The reaction mixture is purged three times with nitrogen while stirring and then heated to 75° C. to 80° C. A pre-mixed feed charge comprising 90 g of EHMA, 54 g of MMA, tert-butanol and 6.5 g of isopropanol is fed in the pump. The feed is started at 70° C. to 80° C. and continued for four hours. The jacket temperature is adjusted to maintain the internal temperature between 75 to 80° C. during the feed. A total amount of 1.35 g of the initial initiator Luperox® 11 is charged in six portions during the feed. After the feed is completed, tert-butanol is used to rinse the feeding line, pump and charge line, and discharged into the reaction vessel. The reaction mixture is maintained on hold for one hour at 75° C. to 80° C. and sampled for analysis by HPLC. The temperature is raised to 80° C.-85° C. An amount of 2.5% by weight of total amount of monomers of chaser initiator Luperox® 11 is charged in six portions every hour. The reaction mixture is maintained on hold for 10 hours at 80° C. to 85° C. The sample is dried under high vacuum at 50° C. to 55° C. In the polymer structure shown, a=20 weight %, b=30 weight % and c=50 weight %.

Example 11: Synthesis of Poly(PyEMA-co-MMA-co-EHMA) with PyEMA/MMA/EHMA Weight Ratio of 20:30:50. Four Hour Feed Reaction in Isopropanol and Tert-Butanol Solvent Combination (40% Solids Process) and Isopropanol Distilled Off at the End

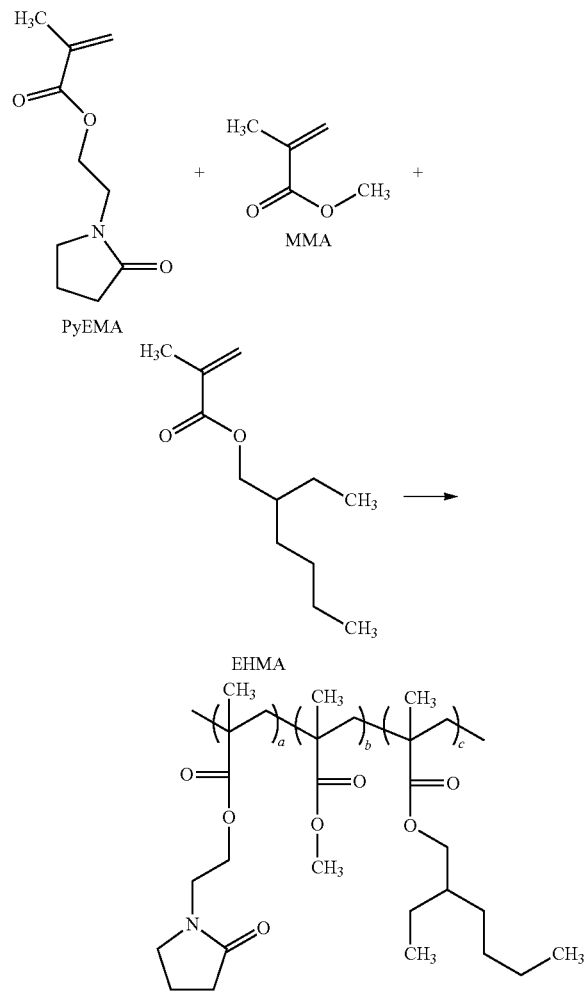

An amount of 36 g of PyEMA, 75 g tert-butanol, and 6.5 g of isopropanol is added to the reaction vessel as a heel charge. The reaction mixture is purged three times with nitrogen while stirring and then heated to 75° C. to 80° C. A pre-mixed feed charge comprising 90 g of EHMA, 54 g of MMA, and tert-butanol is fed in the pump. The feed is started at 70° C. to 80° C. and continued for four hours. The jacket temperature is adjusted to maintain the internal temperature between 75 to 80° C. during the feed. A total amount of 1.35 g of the initial initiator Luperox® 11 is charged in six portions during the feed. After the feed is completed, tert-butanol is used to rinse the feeding line, pump and charge line, and discharged into the reaction vessel. The reaction mixture is maintained on hold for one hour at 75° C. to 80° C. and sampled for analysis by HPLC. The temperature is raised to 80° C.-85° C. and isopropanol removed by atmospheric distillation. An amount of 2.5% by weight of total amount of monomers of chaser initiator Luperox® 11 is charged in six portions. The reaction mixture is maintained on hold for 10 hours at 80° C. to 85° C. The sample is dried under high vacuum at 50° C. to 55° C. In the polymer structure shown, a=20 weight %, b=30 weight % and c=50 weight %.

Example 12: Synthesis of Poly(PyEMA-co-MMA-co-EHMA) with PyEMA/MMA/EHMA Weight Ratio of 20:30:50 (Peroxide/Cu Catalyst Process)

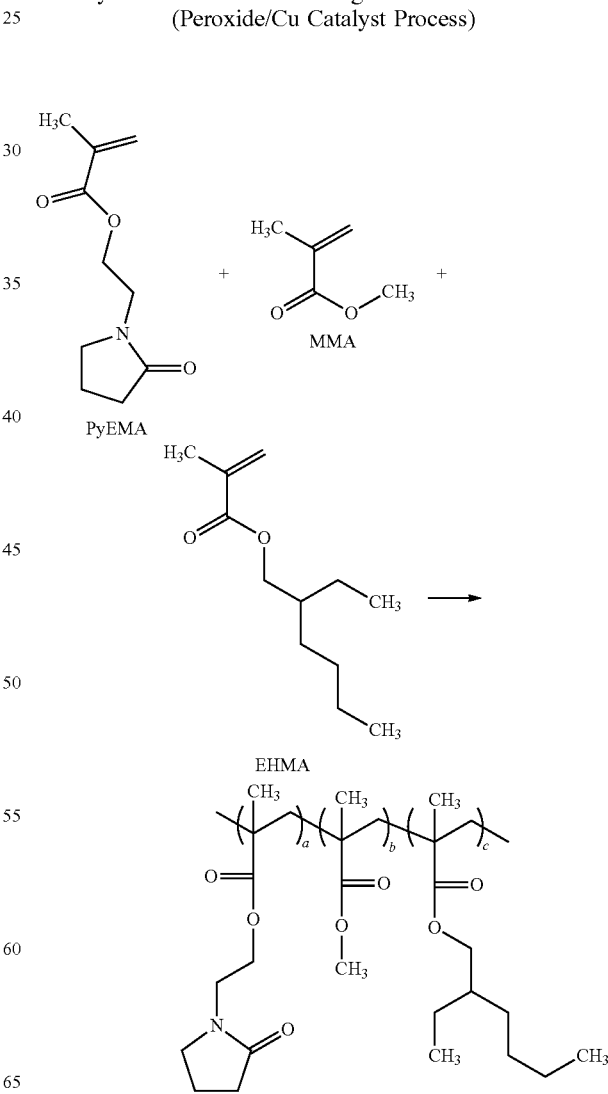

An amount of 36 g of PyEMA, 75 g tert-butanol, 23 g of EHMA and 30 g of isopropanol is added to the reaction vessel as a heel charge. The reaction mixture is purged three times with nitrogen while stirring and then heated to 75° C. to 80° C. A pre-mixed feed charge comprising 67 g of EHMA, 54 g of MMA, tert-butanol and isopropanol is fed in the pump. The feed is started at 70° C. to 80° C. and continued for two hours. The jacket temperature is adjusted to maintain the internal temperature between 75 to 80° C. during the feed. H$_2$O$_2$/Cu catalyst is used as the initial initiator which is charged in six portions during the feed. After the feed is completed, tert-butanol is used to rinse the feeding line, pump and charge line, and discharged into the reaction vessel. The reaction mixture is maintained on hold for one hour at 75° C. to 80° C. and sampled for analysis by HPLC. The temperature is raised to 80° C.-85° C. An amount of 2.5% by weight of total amount of monomers of chaser initiator H$_2$O$_2$/Cu catalyst is charged in six portions. The reaction mixture is maintained on hold for 10 hours at 80° C. to 85° C. The sample is dried under high vacuum at 50° C. to 55° C. In the polymer structure shown, a=20 weight %, b=30 weight % and c=50 weight %.

Example 13: Synthesis of Poly(PyEMA-co-MMA-co-EHMA) with PyEMA/MMA/EHMA Weight Ratio of 20:30:50. EHMA Added Partly in Heel in Tert-Butanol Solvent

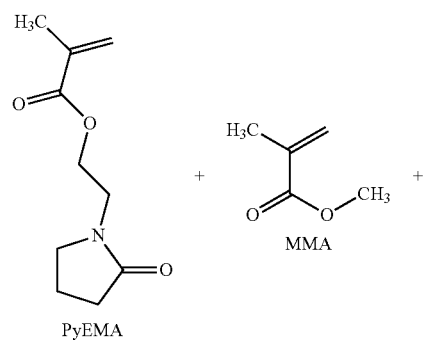

PyEMA

MMA

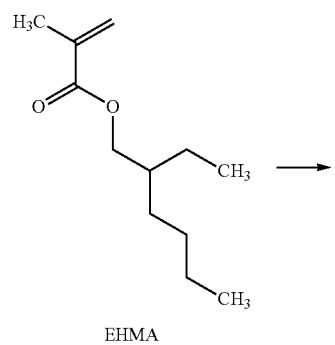

EHMA

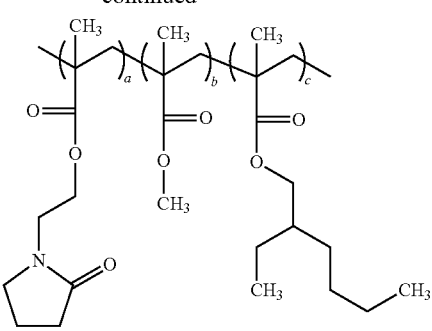

An amount of 36 g of PyEMA, 75 g tert-butanol, and 23 g of EHMA is added to the reaction vessel as a heel charge. The reaction mixture is purged three times with nitrogen while stirring and then heated to 75° C. to 80° C. A pre-mixed feed charge comprising 67 g of EHMA, 54 g of MMA, and tert-butanol is fed in the pump. The feed is started at 70° C. to 80° C. and continued for two hours. The jacket temperature is adjusted to maintain the internal temperature between 80 to 85° C. during the feed. A total amount of 1.35 g of the initial initiator Luperox® 11 is charged in six portions during the feed. After the feed is completed, tert-butanol is used to rinse the feeding line, pump and charge line, and discharged into the reaction vessel. The reaction mixture is maintained on hold for one hour at 80° C. to 85° C. and sampled for analysis by HPLC. An amount of 1.5% by weight of total amount of monomers of chaser initiator Luperox® 11 is charged in three portions in three hours. The reaction mixture is maintained on hold for 10 hours at 80° C. to 85° C. The sample is dried under high vacuum at 50° C. to 55° C. In the polymer structure shown, x=20 weight %, y=30 weight % and z=50 weight %.

Example 14: Synthesis of Poly(PyEMA-co-MMA-co-EHMA) with PyEMA/MMA/EHMA Weight Ratio of 20:30:50. EHMA Added Partly in Heel in Tert-Butanol and Isopropanol Solvent Combination

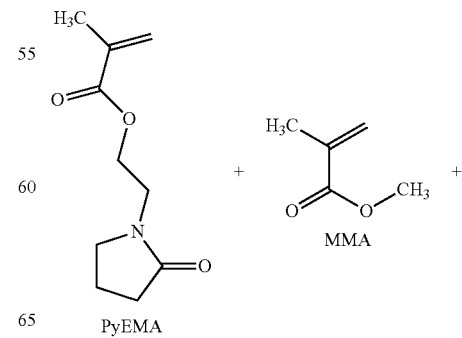

PyEMA

MMA

-continued

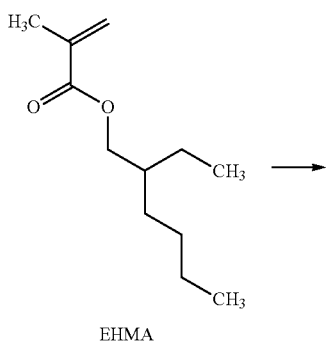

EHMA

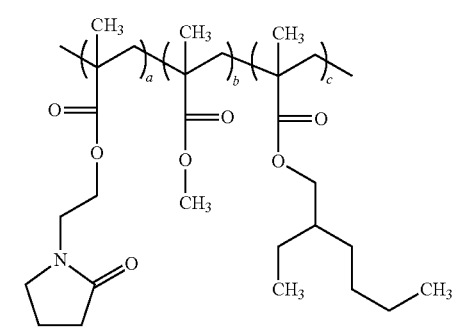

An amount of 36 g of PyEMA, 77 g tert-butanol, 45 g of EHMA, and 33 g of isopropanol is added to the reaction vessel as a heel charge. The reaction mixture is purged three times with nitrogen while stirring and then heated to 70° C. to 75° C. A pre-mixed feed charge comprising 45 g of EHMA, 54 g of MMA, tert-butanol, and isopropanol is fed in the pump. The feed is started at 70° C. to 75° C. and continued for two hours. The jacket temperature is adjusted to maintain the internal temperature between 75 to 80° C. during the feed. A total amount of 1.35 g of the initial initiator Luperox® 11 is charged in three portions during the feed. After the feed is completed, tert-butanol is used to rinse the feeding line, pump and charge line, and discharged into the reaction vessel. The reaction mixture is maintained on hold for one hour at 75° C. to 80° C. and sampled for analysis by HPLC. The temperature is raised to 120° C.-130° C. An amount of 1.5% by weight of total amount of monomers of chaser initiator Luperox® 101 is charged in six portions. The reaction mixture is maintained on hold for six hours at 120° C. to 130° C. The sample is dried under high vacuum at 50° C. to 55° C. In the polymer structure shown, a=20 weight %, b=30 weight % and c=50 weight %.

Example 15: Synthesis of Poly(PyEMA-co-MMA-co-EHMA) with PyEMA/MMA/EHMA Weight Ratio of 20:30:50. EHMA Added Partly in Heel in n-Heptane Solvent

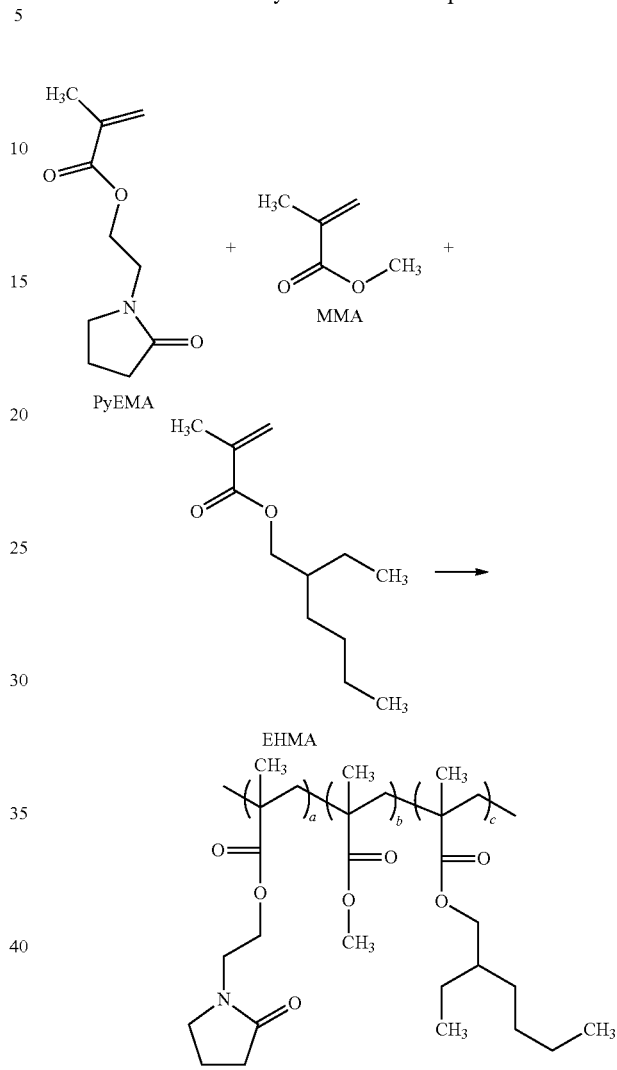

An amount of 36 g of PyEMA, 38 g n-heptane, 36 g of EHMA, and 0.5 g of Vazo® 67 is added to the reaction vessel as a heel charge. The reaction mixture is purged three times with nitrogen while stirring and then heated to 80° C. to 85° C. A pre-mixed feed charge comprising 54 g of EHMA, 54 g of MMA, and n-heptane is fed in the pump. The feed is started at 70° C. to 75° C. and continued for two hours. The jacket temperature is adjusted to maintain the internal temperature between 75 to 80° C. during the feed. After the feed is completed, n-heptane is used to rinse the feeding line, pump and charge line, and discharged into the reaction vessel. The reaction mixture is maintained on hold for one hour at 75° C. to 80° C. and sampled for analysis by HPLC. The temperature is raised to 85° C.-90° C. An amount of 2.0% by weight of total amount of monomers of chaser initiator Luperox® 121 is charged in four portions. The reaction mixture is maintained on hold for 10 hours at 90° C. The sample is dried under high vacuum at 50° C. to 55° C. In the polymer structure shown, a=20 weight %, b=30 weight % and c=50 weight %.

Example 16: Synthesis of Poly(PyEMA-co-MMA-co-EHMA) with PyEMA/MMA/EHMA Weight Ratio of 20:30:50. EHMA Added Partly in Heel in Ceraphyl® 230

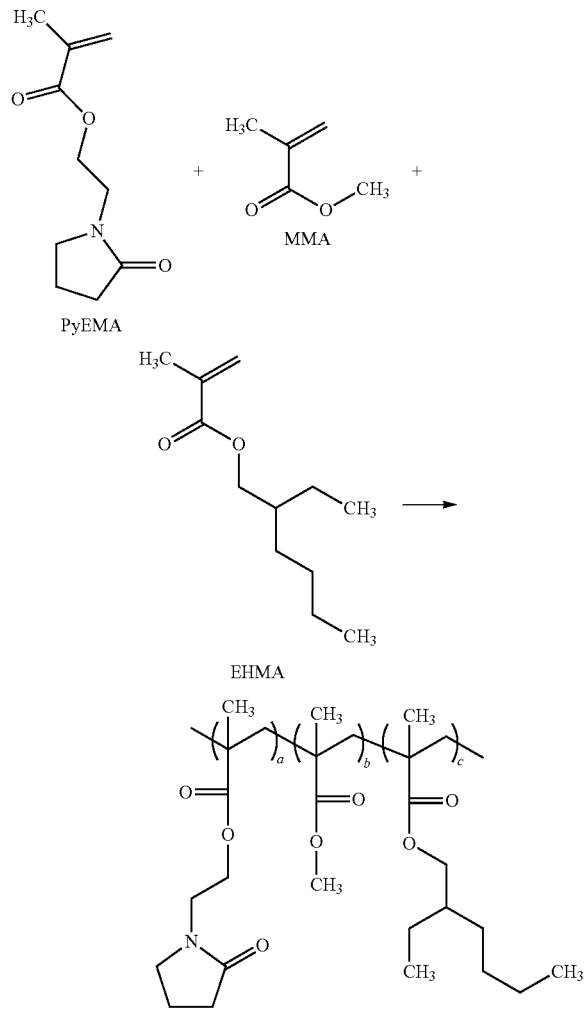

An amount of 36 g of PyEMA, 39 g Ceraphyl® 230, 36 g of EHMA, and 0.9 g of Luperox® 11 is added to the reaction vessel as a heel charge. The reaction mixture is purged three times with nitrogen while stirring and then heated to 80° C. to 85° C. A pre-mixed feed charge comprising 54 g of EHMA, 54 g of MMA, and Ceraphyl® 230 is fed in the pump. The feed is started at 70° C. to 75° C. and continued for two hours. The jacket temperature is adjusted to maintain the internal temperature between 75 to 80° C. during the feed. After the feed is completed, Ceraphyl® 230 is used to rinse the feeding line, pump and charge line, and discharged into the reaction vessel. The reaction mixture is maintained on hold for one hour and sampled for analysis by HPLC. An amount of 2.0% by weight of total amount of monomers of chaser initiator Luperox® 11 is charged in four portions. The reaction mixture is maintained on hold for 10 hours at 80° C. to 85° C. The sample is dried under high vacuum at 50° C. to 55° C. In the polymer structure shown, a=20 weight %, b=30 weight % and c=50 weight %.

Example 17: Synthesis of Poly(PyEMA-co-MMA-co-EHMA) with PyEMA/MMA/EHMA Weight Ratio of 20:30:50. EHMA not Added in Heel. Ceraphyl® 230 Solvent

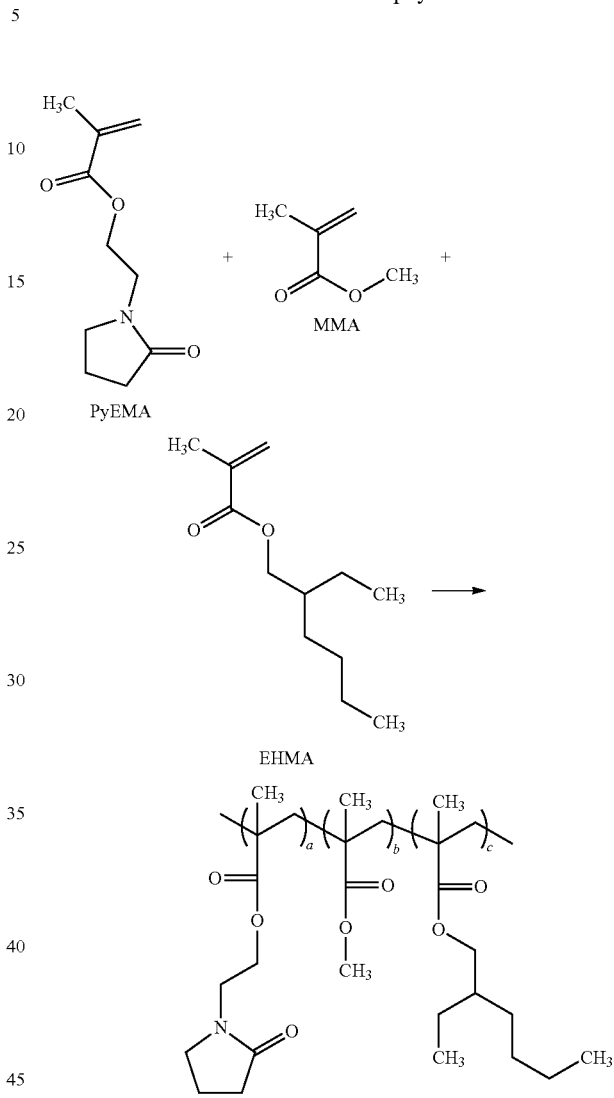

An amount of 36 g of PyEMA, 75 g Ceraphyl® 230 and 0.9 g of Luperox® 11 is added to the reaction vessel as a heel charge. The reaction mixture is purged three times with nitrogen while stirring and then heated to 80° C. to 85° C. A pre-mixed feed charge comprising 90 g of EHMA, 54 g of MMA, and Ceraphyl® 230 is fed in the pump. The feed is started at 70° C. to 75° C. and continued for two hours. The jacket temperature is adjusted to maintain the internal temperature between 75 to 80° C. during the feed. After the feed is completed, Ceraphyl® 230 is used to rinse the feeding line, pump and charge line, and discharged into the reaction vessel. The reaction mixture is maintained on hold for one hour and sampled for analysis by HPLC. An amount of 2.0% by weight of total amount of monomers of chaser initiator Luperox® 11 is charged in four portions. The reaction mixture is maintained on hold for 10 hours at 80° C. to 85° C. The sample is dried under high vacuum at 50° C. to 55° C. In the polymer structure shown, a=20 weight %, b=30 weight % and c=50 weight %.

Sun Care Application

Non-aqueous sun care compositions according to the invention can be tested for water resistance using an in-vitro method as described below:

In-Vitro Water Resistance (1) VITRO-SKIN® (VS) is cut into 3.0 cm×4.0 cm strips and mounted in place in a 35 mm slide holder.

(2) Four slides are made for each test product.

(3) One slide is made for the blank, to obtain the baseline and zero readings.

(4) The slides are then placed into a hydration chamber for 12-14 hours to allow the VS to hydrate. The relative humidity of the chamber is maintained by an 18% w/w glycerin solution.

(5) An amount of 6 to 7 mg of the test product is applied to each strip of VS. The slide is then placed back in the humidity chamber for 20 minutes to allow for coalescence of the test product.

(6) The initial UV absorbance of each slide is measured with a UV-Visible spectrophotometer (Cary 300 Series) in the wavelength range of 290-400 nm.

(7) Two readings are taken for each slide—one from each end.

(8) The slides are then immersed in a 25° C. water bath, with circulation of 90 rpm for 80 minutes.

The slides are then removed and allowed to air dry for 15 minutes.

(9) The slides are equilibrated in the humidity chamber for 120 minutes, and the absorbance post immersion is calculated.

(10) The initial and post absorbance data is saved as a spreadsheet and exported to an Excel spreadsheet.

(11) Area under the curve (sum of the y value) from 290-400 nm is calculated for each reading. This is done for both initial readings and post immersion readings.

(12) The percent water resistance is calculated from the following equation:

Percent Water Resistance=(Absorbance post immersion/Initial Absorbance)×100.

The average value of four slides gives the final percent water resistance.

Sun Care Emulsion I

TABLE 1

List of components of Sun Care Emulsion I

| Phase | Ingredient | Trade Name (manufacturer) | Composition, % w/w |
|---|---|---|---|
| A | Water | | 52.65 |
| | Phenoxyethanol (and) Methylparaben (and) Ethylparaben (and) Propylparaben | Rokonsal ™/LiquaPar ™ MEP preservative (Ashland Inc.) | 1.00 |
| | Triethanolamine | Triethanolamine (Dow) | 0.15 |
| | Acrylic Acid/VP Crosspolymer | UltraThix ™ P-100 polymer (Ashland) | 0.40 |
| B | Avobenzone | Escalol ™ 517 UV filter (Ashland) | 3.00 |
| | Octisalate | Escalol ™ 587 UV filter (Ashland) | 5.00 |
| | Homosalate | Escalol ™ HMS UV filter (Ashland) | 8.00 |
| | Octocrylene | Escalol ™ 597 UV filter (Ashland) | 5.00 |
| | Benzopheneone-3 | Escalol ™ 567 UV filter (Ashland) | 6.00 |
| | Glyceryl Stearate (and) PEG-100 Stearate | Arlacel ™ 165 (Croda) | 4.00 |
| | Diisopropyl Adipate | Ceraphyl ™ 230 ester (Ashland) | 5.50 |
| | C12-15 Alkyl Lactate | Ceraphyl ™ 41 ester (Ashland) | 2.50 |
| | Glyceryl Dilaurate | Emulsynt ™ GDL emulsifier (Ashland) | 0.50 |
| | Stearyl Alcohol | | 1.00 |
| C | Glycerin (and) Glyceryl Polyacrylate | Lubrajel ™ II-XD (Ashland) | 1.00 |
| | Cyclopentasiloxane | Si-Tec CM040 | 3.00 |
| D | Phenoxyethanol (and) Methylisothiozolinone | Optiphen ™ MIT Ultra (Ashland) | 0.30 |
| | Total | | 99.0 |

An amount of 1.0 g of the film forming polymer prepared according to Example 1 is added to Phase B of Sun Care Emulsion I and the resulting emulsion is tested for water resistance. FIG. 1 shows the percent water resistance value of the emulsion comprising polymer of Example 1 in comparison with various commercially available sun care products.

Sun Care Emulsion II

TABLE 2

List of components of Sun Care Emulsion II

| Phase | Ingredient | Trade Name (manufacturer) | Composition, % w/w |
|---|---|---|---|
| A | Water | | 51.60 |
| | Glycerin | Glycerin (Ruger) | 1.00 |
| | Phenoxyethanol (and) Methylparaben (and) Ethylparaben (and) Propylparaben | LiquaPar™ MEP preservative (Ashland) | 1.00 |
| | Carbomer | Carbomer™ 980 (Ashland) | 0.30 |
| B | Avobenzone | Escalol™ 517 UV filter (Ashland) | 3.00 |
| | Octisalate | Escalol™ 587 UV filter (Ashland) | 5.00 |
| | Homosalate | Escalol™ HMS UV filter (Ashland) | 8.00 |
| | Octocrylene | Escalol™ 597 UV filter (Ashland) | 5.00 |
| | Benzopheneone-3 | Escalol™ 567 UV filter (Ashland) | 6.00 |
| | Glyceryl Stearate (and) PEG-100 Stearate | Arlacel™ 165 (Croda) | 4.00 |
| | Diisopropyl Adipate | Ceraphyl™ 230 ester (Ashland) | 5.50 |
| | C12-15 Alkyl Lactate | Ceraphyl™ 41 ester (Ashland) | 2.50 |
| | Glyceryl Dilaurate | Emulsynt™ GDL emulsifier (Ashland) | 0.50 |
| | Stearyl Alcohol | | 1.00 |
| | Triethanolamine | Triethanolamine (Dow) | 0.30 |
| C | Glycerin (and) Glyceryl Polyacrylate | Lubrajel™ II-XD (Ashland) | 1.00 |
| | Cyclopentasiloxane | Si-Tec CM040 | 3.00 |
| D | Phenoxyethanol (and) Methylisothiozolinone | Optiphen™ MIT Ultra (Ashland) | 0.30 |
| | Total | | 99.0 |

Figure 2:
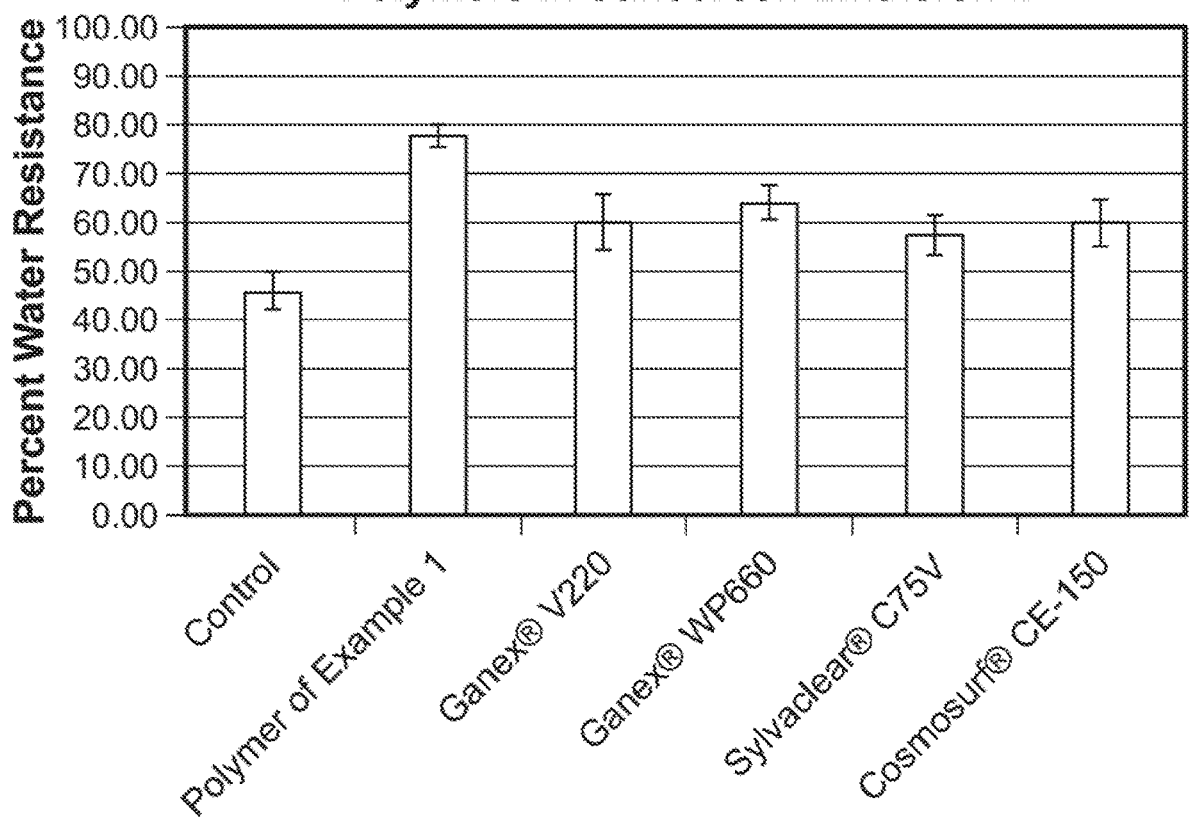
FIG. 2 shows the percent water resistance study of non-aqueous sun care formulations according to the invention in comparison with various commercially available formulations.

An amount of 1.0 g of the film forming polymer prepared according to Example 1 is added to Phase B of Sun Care Emulsion II and the resulting emulsion is tested for water resistance. FIG. 2 shows the percent water resistance of the emulsion comprising polymer of Example 1 in comparison with various commercially available sun care products.

Sun Care Emulsion III

TABLE 3

List of components of Sun Care Emulsion III

| Phase | Ingredient | Trade Name (manufacturer) | Composition, % w/w |
|---|---|---|---|
| A | Water | | 55.70 |
| | Glycerin | Glycerin (Ruger) | 2.00 |
| | Xanthan Gum | | 0.50 |
| B | Avobenzone | Escalol™ 517 UV filter (Ashland) | 3.00 |
| | Octisalate | Escalol™ 587 UV filter (Ashland) | 5.00 |
| | Homosalate | Escalol™ HMS UV filter (Ashland) | 8.00 |
| | Octocrylene | Escalol™ 597 UV filter (Ashland) | 5.00 |
| | Benzopheneone-3 | Escalol™ 567 UV filter (Ashland) | 6.00 |
| | Glyceryl Stearate (and) PEG-100 Stearate | Arlacel™ 165 (Croda) | 4.00 |
| | Diisopropyl Adipate | Ceraphyl™ 230 ester (Ashland) | 5.50 |
| | C12-15 Alkyl Lactate | Ceraphyl™ 41 ester (Ashland) | 2.50 |
| | Glyceryl Dilaurate | Emulsynt™ GDL emulsifier (Ashland) | 0.50 |
| | Stearyl Alcohol | | 1.00 |
| C | Phenoxyethanol (and) Methylisothiozolinone | Optiphen™ MIT Ultra (Ashland) | 0.30 |
| | Total | | 99.0 |

Figure 3:
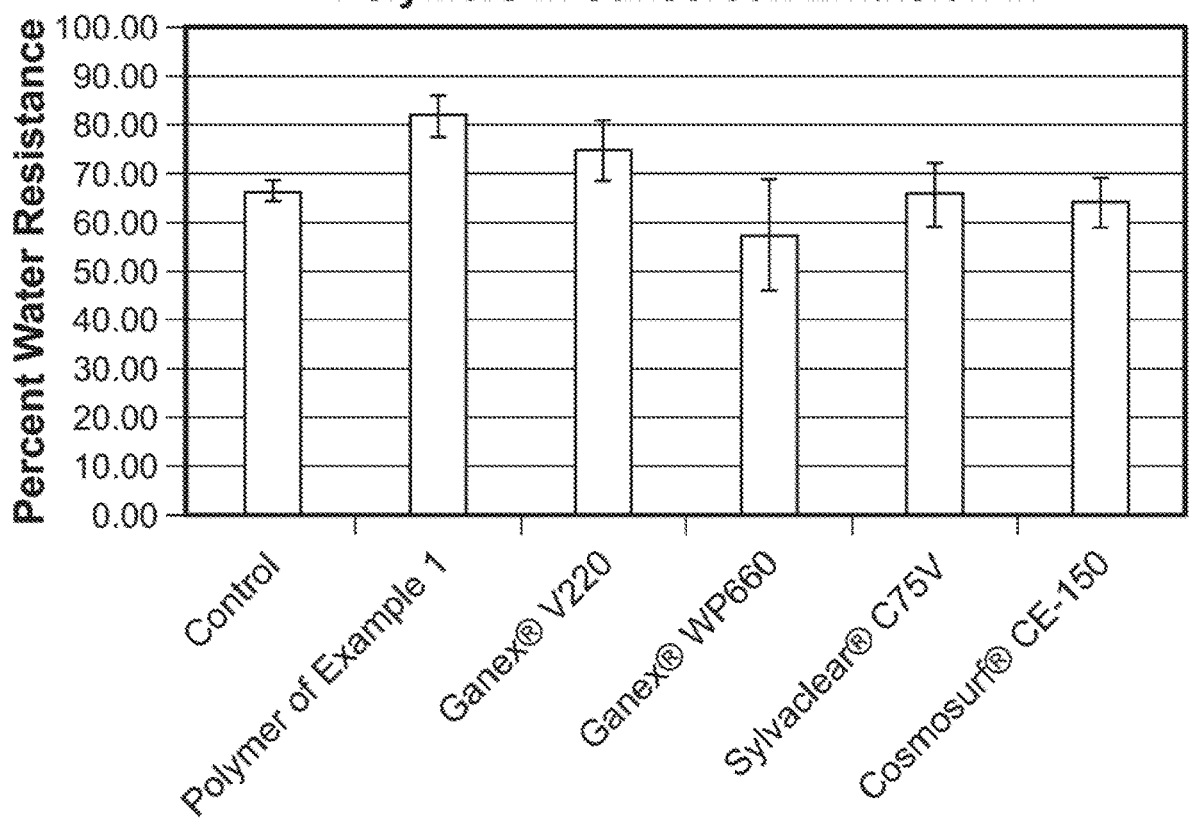
FIG. 3 shows the percent water resistance study of non-aqueous sun care formulations according to the invention in comparison with various commercially available formulations.

An amount of 1.0 g of the film forming polymer prepared according to Example 1 is added to Phase B of Sun Care Emulsion III and the resulting emulsion is tested for water resistance. FIG. 3 shows the percent water resistance of the emulsion comprising polymer of Example 1 in comparison with various commercially available sun care products.

Anhydrous Formulation

TABLE 4

List of components of Anhydrous Formulation

| Phase | Ingredient | Trade Name (manufacturer) | Composition, % w/w |
|---|---|---|---|
| A | Ethanol | | 66.00 |
| B | Avobenzone | Escalol ™ 517 UV filter (Ashland) | 3.00 |
| | Octisalate | Escalol ™ 587 UV filter (Ashland) | 5.00 |
| | Homosalate | Escalol ™ HMS UV filter (Ashland) | 10.00 |
| | Octocrylene | Escalol ™ 597 UV filter (Ashland) | 10.00 |
| | Benzopheneone-3 | Escalol ™ 567 UV filter (Ashland) | 5.00 |
| | Total | | 99.0 |

Figure 4:
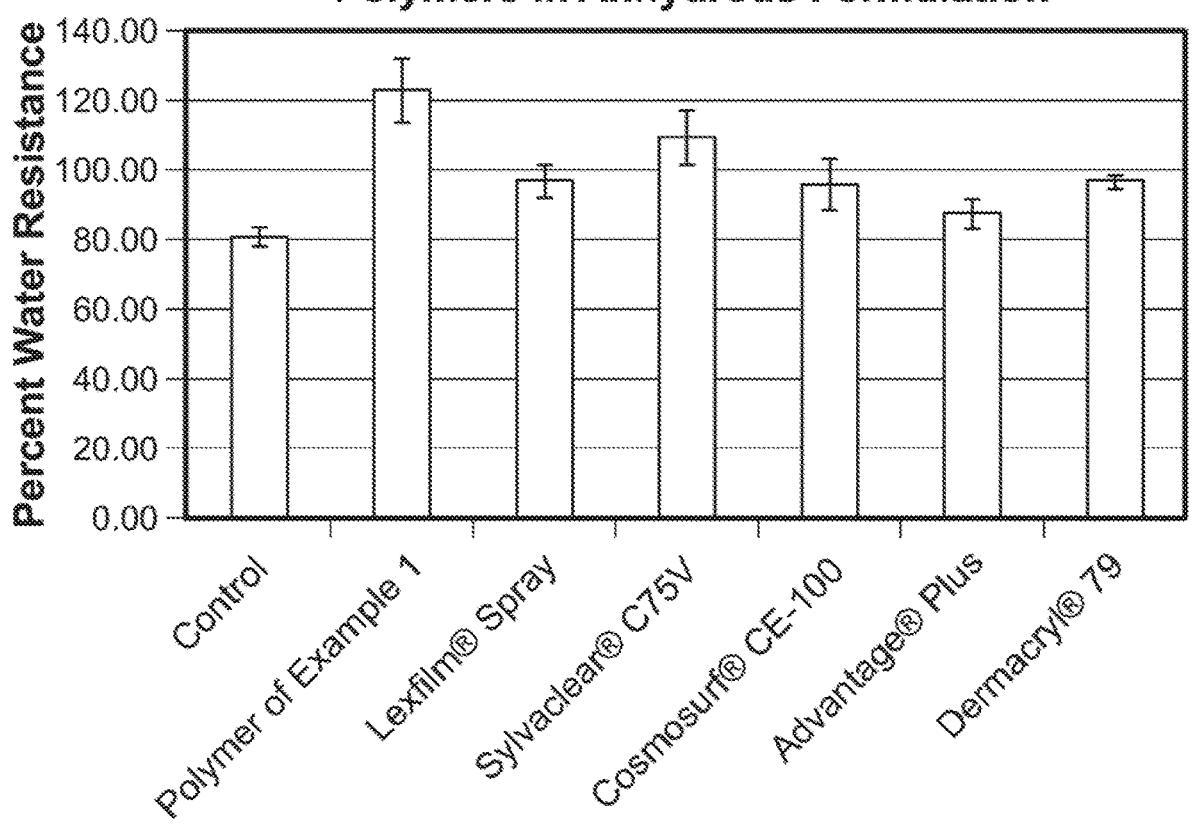
FIG. 4 shows the percent water resistance study of non-aqueous sun care formulations according to the invention in comparison with various commercially available formulations.
Figure 5:
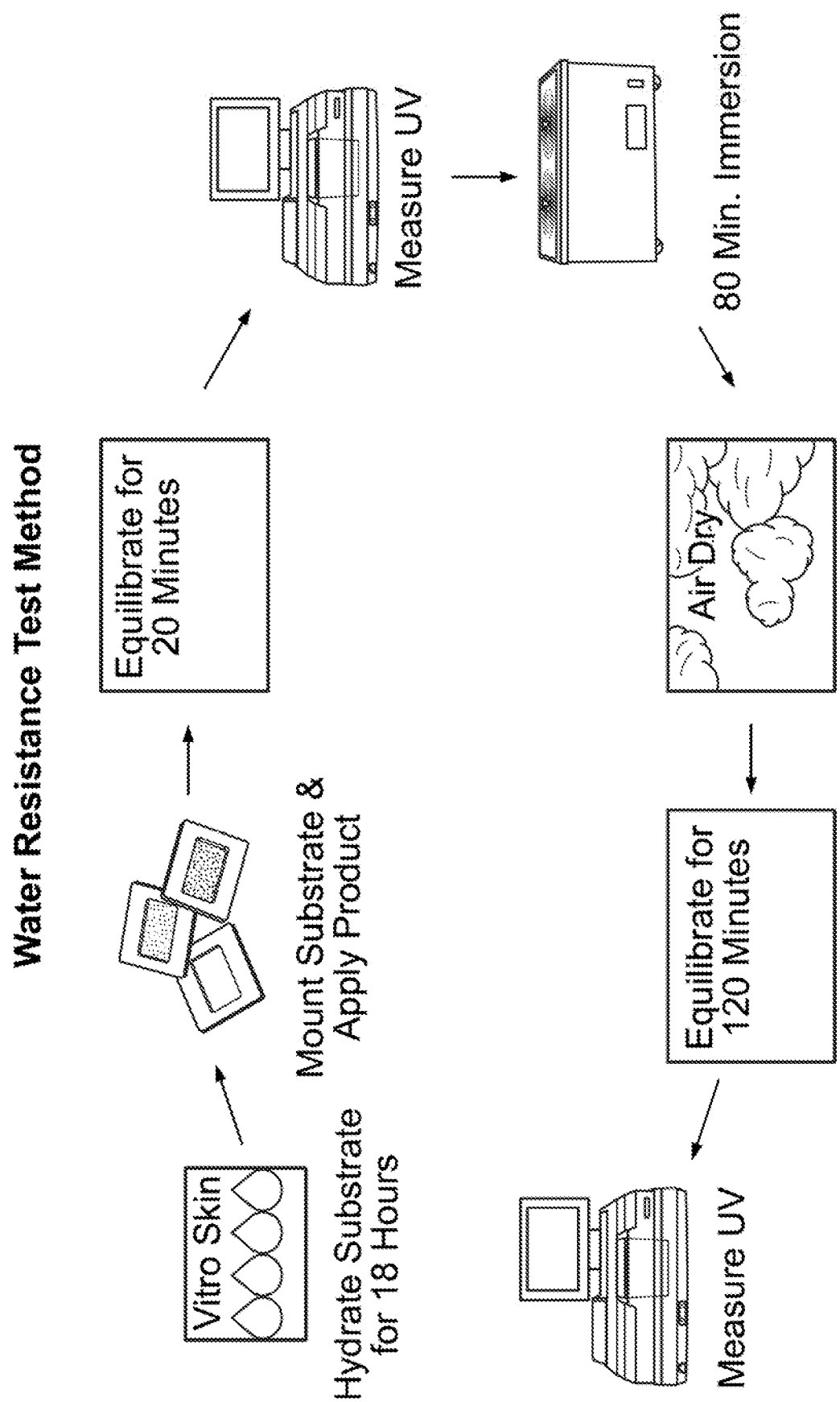
FIG. 5. shows the in-vitro water resistance test method

An amount of 1.0 g of the film forming polymer prepared according to Example 1 is added to Phase B of the Anhydrous Formulation and the resulting formulation is tested for water resistance. FIG. 4 shows the percent water resistance of the Anhydrous Formulation comprising polymer of Example 1 in comparison with various commercially available sun care products.

All references including patent applications and publication cited herein are incorporated herein by reference in their entirety and for all purpose to the same extent as if each individual publication or patent or patent application was specifically and individually indicated to be incorporated by reference in its entirety for all purposes. Many modifications and variations of the presently disclosed and claimed inventive concept(s) can be made without departing from its spirit and scope, as will be apparent to those skilled in the art.

What is claimed is:

1. A non-aqueous composition comprising a film forming polymer comprising repeating units derived from at least:
   (a) from about 10 to about 40 percent by weight of said polymer of at least one monomer having a structure selected from the group consisting of:

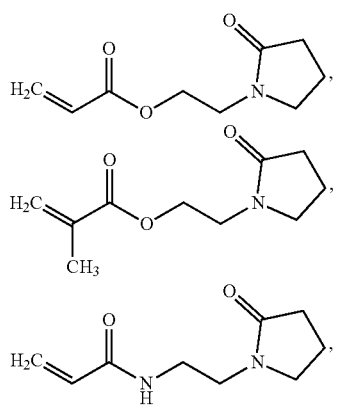

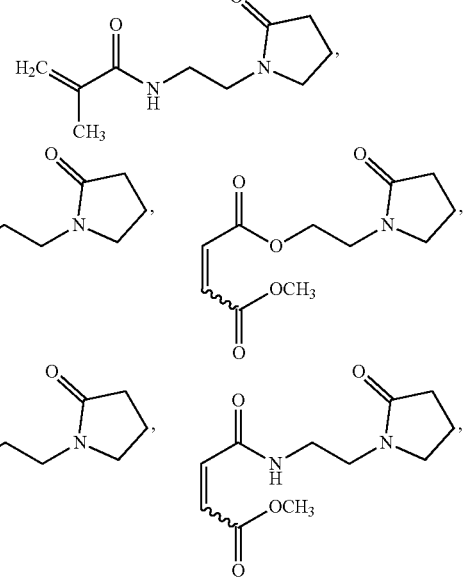

and combinations thereof;
   (b) from about 15 to about 45 percent by weight of said polymer of at least one monomer selected from the group consisting of methyl acrylate, methyl methacrylate, methyl acrylamide, methyl methacrylamide, and combinations thereof; and
   (c) from about 25 to about 75 percent by weight of said polymer of at least one monomer selected from the group consisting of 2-ethylhexyl acrylate, 2-ethylhexyl methacrylate, N-2-ethylhexyl acrylamide, N-2-ethylhexyl methacrylamide, and combinations thereof.

2. A non-aqueous composition comprising a film forming polymer having a structure selected from the group consisting of:

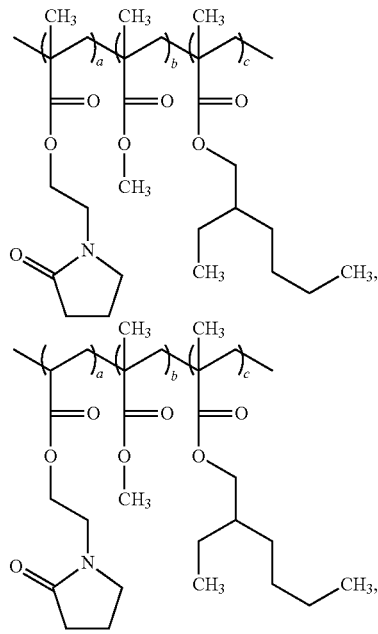

61
-continued
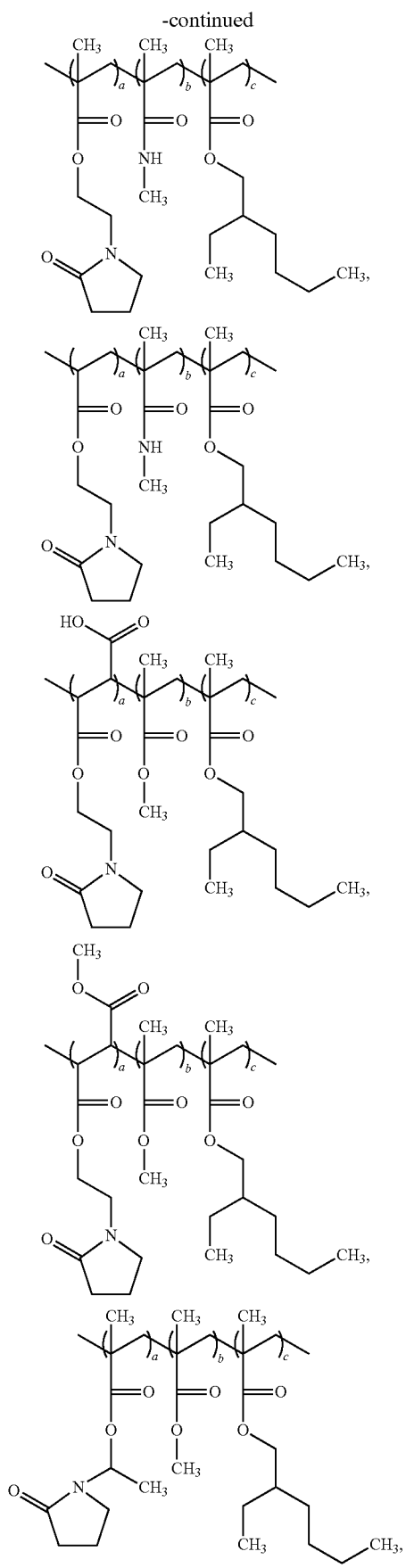
62
-continued
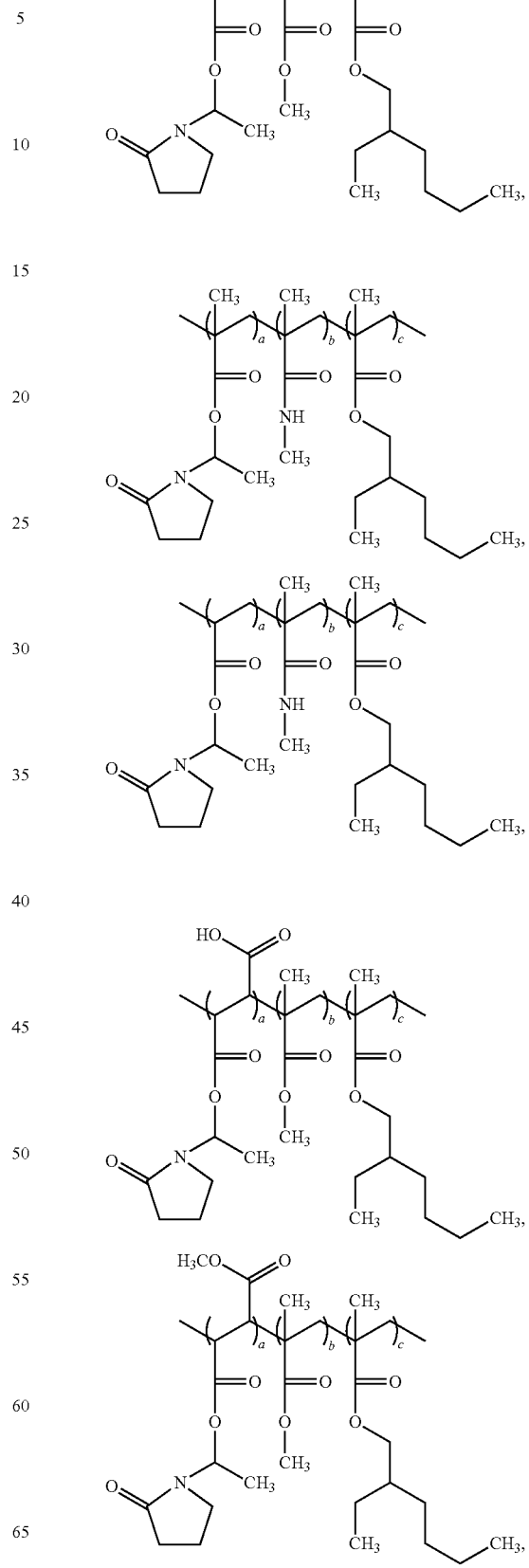

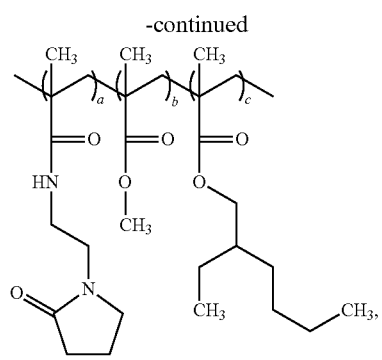
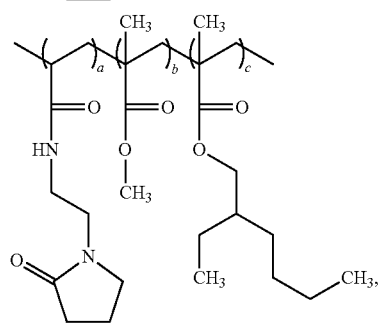
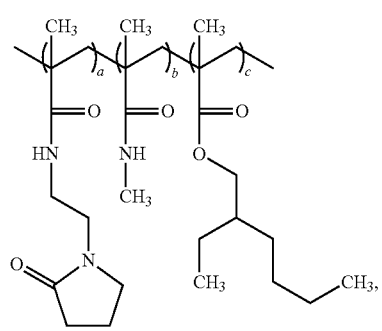
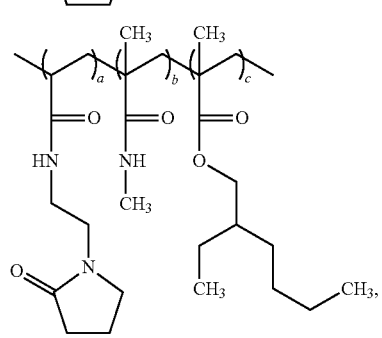
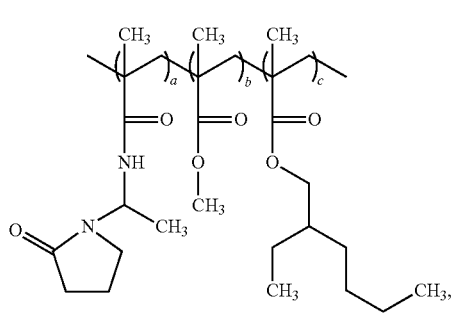
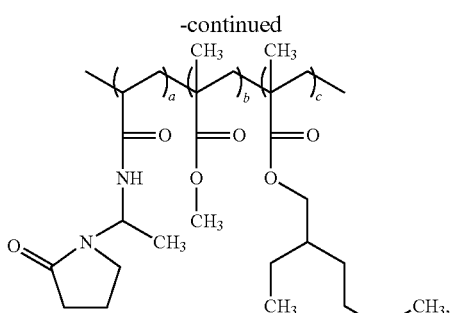
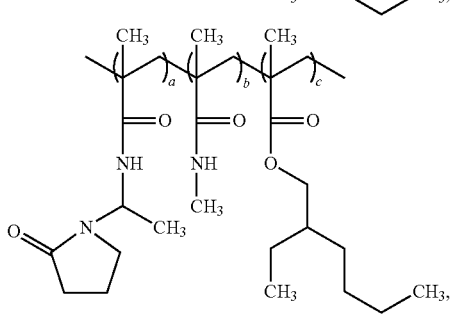
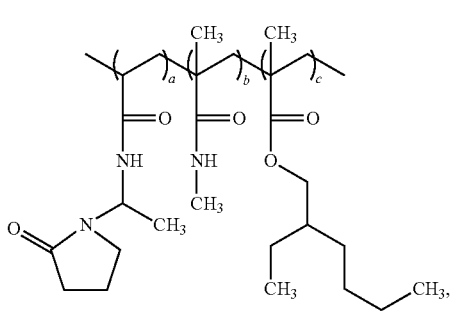
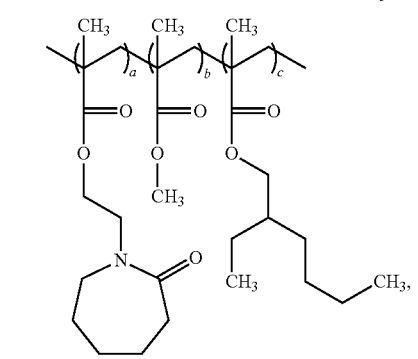
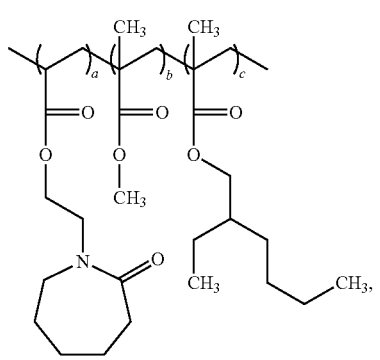

65
-continued
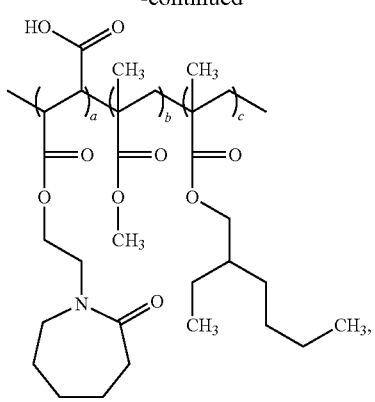
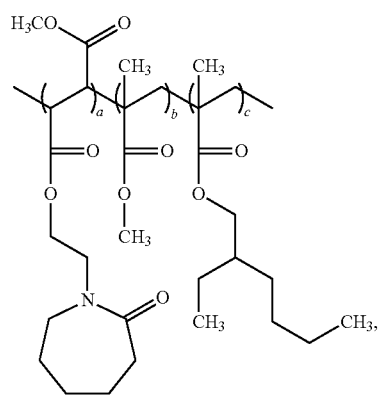
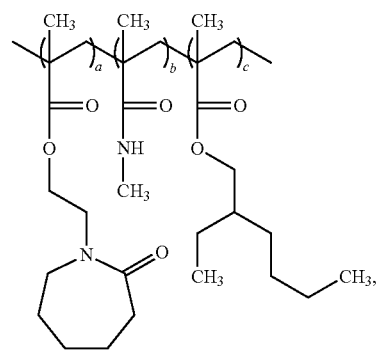
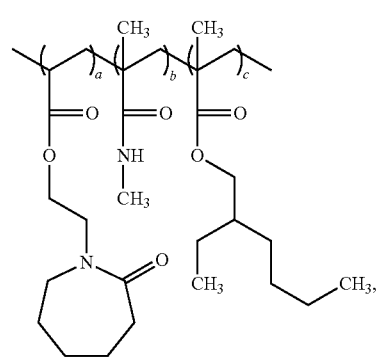
66
-continued
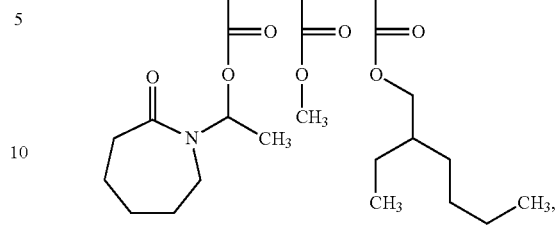
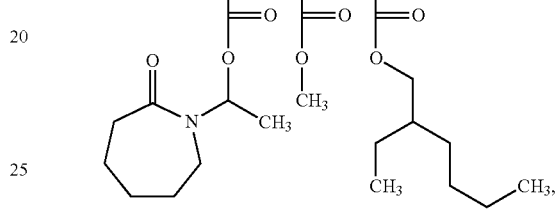
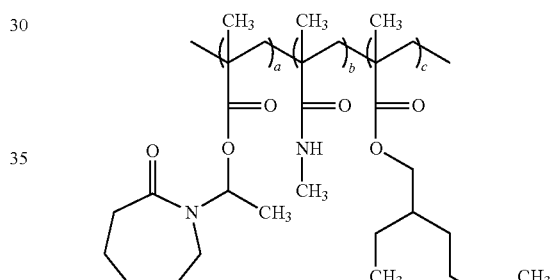
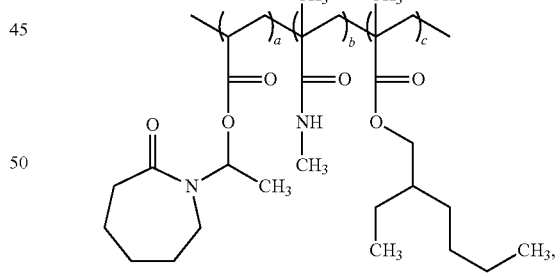
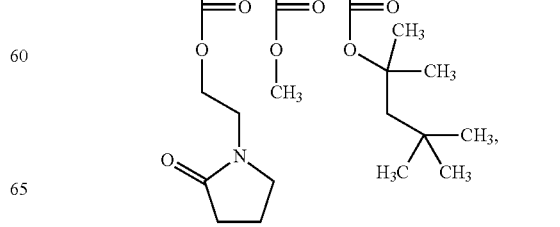

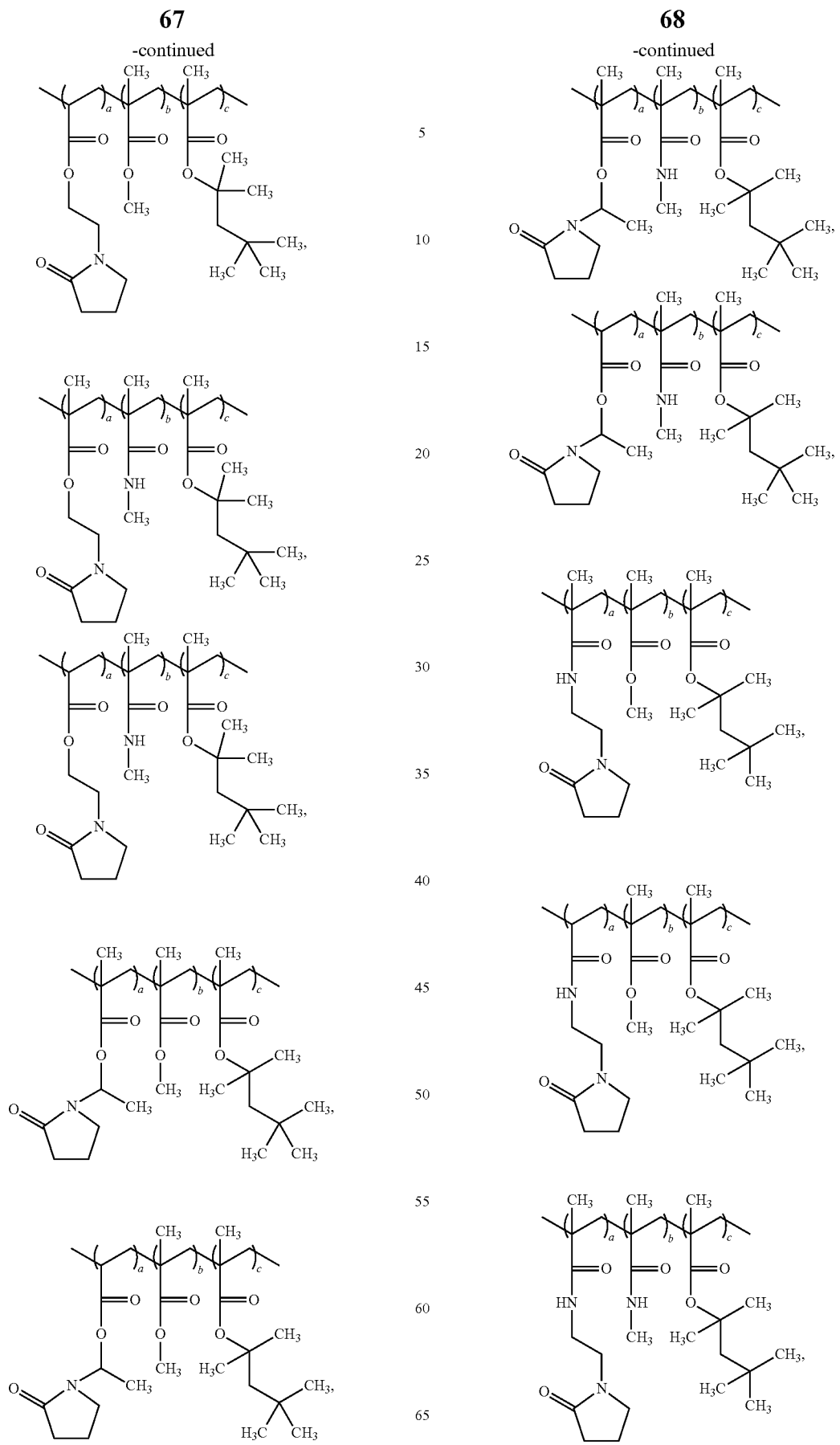

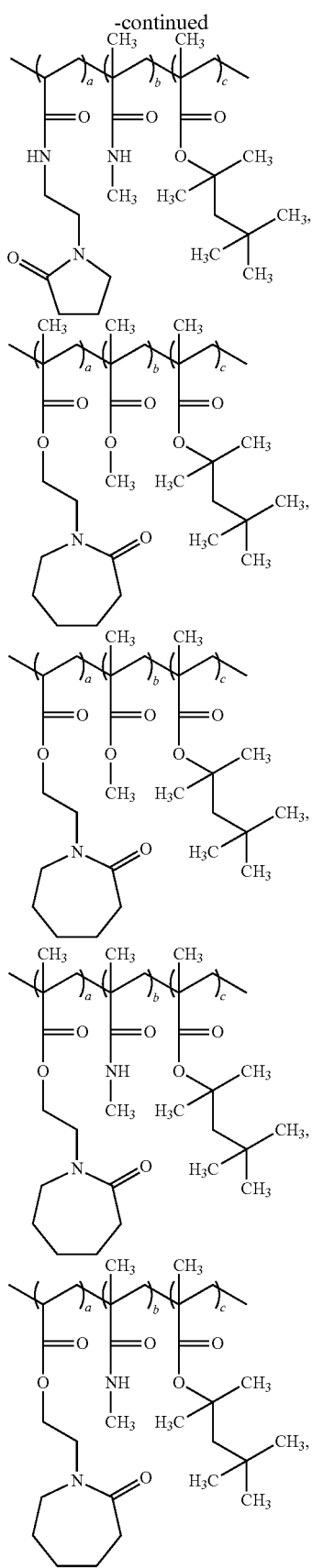
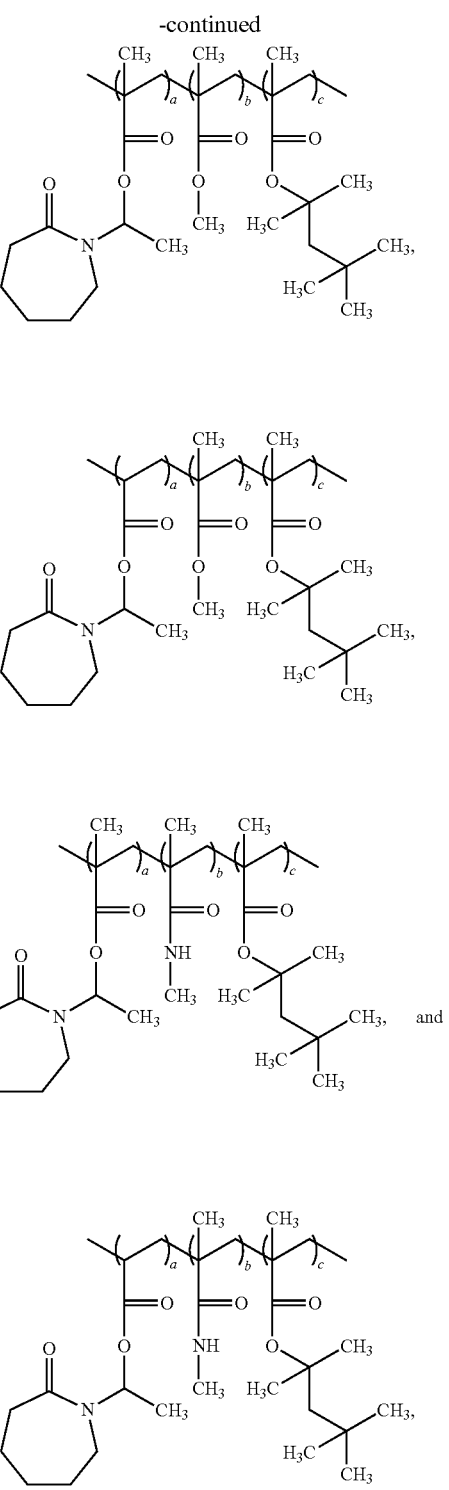
wherein each a, b and c is an independently selected value ranging from about 0.1 to about 99.9 percent by weight of said polymer, with the proviso that sum of said a, b and c for each said polymer equals 100 weight percent.
* * * * *